United States Patent [19]
Yasutomi et al.

[11] Patent Number: 5,581,039
[45] Date of Patent: Dec. 3, 1996

[54] CERAMIC BODY AND METHOD AND APPARATUS FOR DETECTING CHANGE THEREOF

[75] Inventors: Yoshiyuki Yasutomi, Mito; Motoyuki Miyata, Hitachi; Shigeru Kikuchi, Naka-machi; Yukio Saito, Hitachi, all of Japan

[73] Assignee: Hitachi, Ltd., Tokyo, Japan

[21] Appl. No.: 339,877

[22] Filed: Nov. 10, 1994

Related U.S. Application Data

[62] Division of Ser. No. 123,187, Sep. 17, 1993, abandoned.

[30] Foreign Application Priority Data

Sep. 18, 1992  [JP]  Japan ..................... 4-249941

[51] Int. Cl.⁶ ................................. G01N 33/20
[52] U.S. Cl. ........................................ 73/768
[58] Field of Search .................... 73/763, 764, 766, 73/767, 768, 774, 775, 776, 799

[56] References Cited

U.S. PATENT DOCUMENTS

| | | | |
|---|---|---|---|
| 3,080,748 | 3/1963 | Burkley | 73/768 |
| 3,453,873 | 7/1969 | Lambert | 73/775 |
| 3,779,071 | 12/1973 | Thomas et al. | 73/767 |
| 3,803,485 | 4/1974 | Gutes et al. | 73/763 |
| 3,950,984 | 4/1976 | Russell | 73/774 |
| 4,090,162 | 5/1978 | Cardone et al. | 335/209 |
| 4,341,965 | 7/1982 | Okuo et al. | 501/95 |
| 4,379,195 | 4/1983 | Prabhu et al. | 427/126.2 |
| 4,744,252 | 5/1988 | Stout | 73/768 |
| 4,808,076 | 2/1989 | Jarmon et al. | 501/95 |
| 4,945,770 | 8/1990 | Alvelid et al. | 73/768 |
| 4,961,990 | 10/1990 | Yamada | 501/95 |
| 5,130,055 | 7/1992 | Yasutomi et al. | 501/95 |
| 5,184,516 | 2/1993 | Blazic et al. | 73/767 |
| 5,379,644 | 1/1995 | Yanagidar et al. | 73/768 |

FOREIGN PATENT DOCUMENTS

| | | |
|---|---|---|
| 57-113360 | 7/1982 | Japan . |
| 59-3335 | 1/1984 | Japan . |

OTHER PUBLICATIONS

"$Si_3N_4$–SiC Whisker Based Composite Ceramics", Ceramic No. 12, (1983), pp. 1040–1046.

"Non–Destructive Evaluation Technique for Ceramics", Ceramics No. 10, (1985), pp. 879–884.

*Primary Examiner*—Richard Chilcot
*Assistant Examiner*—George M. Dombroske
*Attorney, Agent, or Firm*—Antonelli, Terry, Stout & Kraus

[57] ABSTRACT

To provide diagnosis of service life and maintenance requirements, a sintered ceramic body which in use is subjected to stress and undergoes change with time as a result of the stress is provided with an electrically conductive element in contact with the sintered ceramic material The element has a measurable electrical resistance which increases in dependence on the change of the ceramic body. This permits information to be obtained about said change of said body. Measuring means for the electrical resistance is connected to the conductive element. The electrically conductive element as seen in cross-section, may comprise a bundle of elongate members such as fibers or whiskers.

15 Claims, 17 Drawing Sheets

FIG. 24
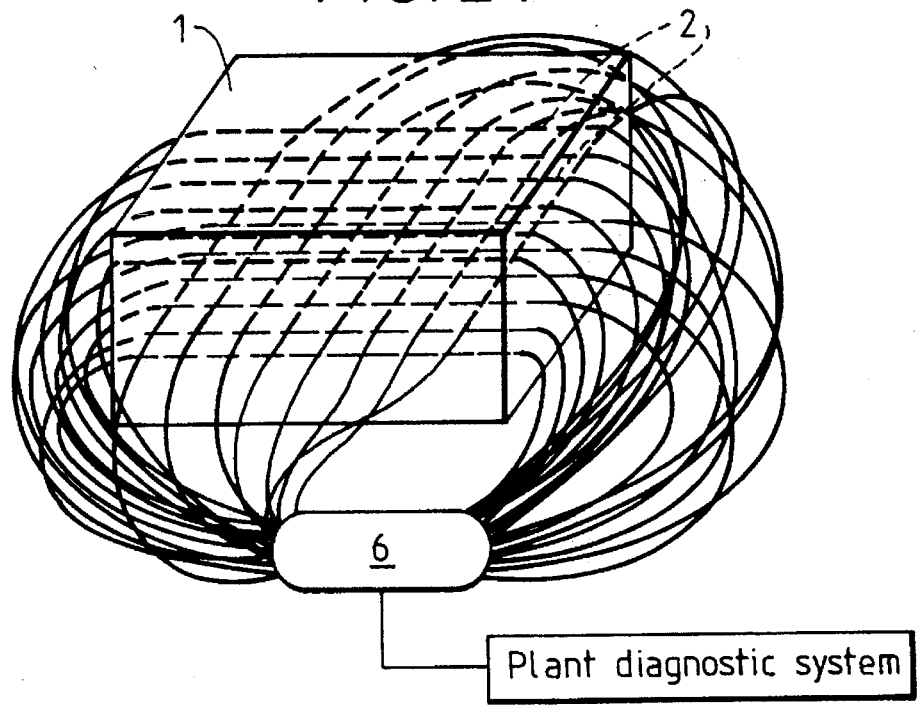
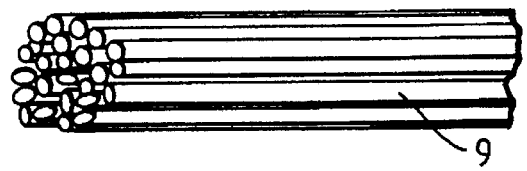
FIG. 25
FIG. 26
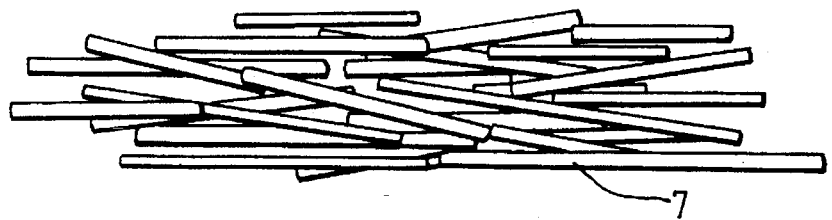

CERAMIC BODY AND METHOD AND APPARATUS FOR DETECTING CHANGE THEREOF

This application is a divisional of application Ser. No. 08/123,187, filed on Sep. 17, 1993, now abandoned.

BACKGROUND OF THE INVENTION

1. Field of the Invention

This invention relates to ceramic bodies which in use are subjected to stress, and to methods and apparatus for monitoring changes caused by subjecting ceramic bodies to stress in use. The invention can provide a diagnostic method and apparatus for estimating the remaining useful working life of a ceramic body.

2. Description of the Prior Art

One of the biggest problems in application of structural ceramics to actual working parts lies in their low reliability. A ceramic can be superior to a metal in resistance against heat, acid and abrasion, but is less reliable because of low fracture toughness (poor tenacity), creating problems which make it difficult to use the ceramic as structural parts. Many methods of improving toughness (e.g. "$Si_3N_4$—SiC Whisker Based Composite Ceramics," Ceramics No.12, 1983) or a method of confirming the development of cracks ("Non-Destructive Evaluation Technique for Ceramics," Ceramics No.10, 1985) by means of ultra-sonic waves have been proposed to solve these problems.

To determine the maintenance period for a gas turbine plant, for example, the service life is calculated (JP-A-59-3335), or the service life of a test piece placed close to the actual machine part is measured for diagnosis (JP-A-57-113360). All these methods fail to diagnose the state of the actual machine part directly, and cannot be called precise life diagnostic methods.

The prior art discussed above therefore does not diagnose the service life of the actual machine part directly, leaving much room for improvement in reliability prediction and life diagnosis. This is because, despite particle dispersion and fiber reinforcement, the efforts for improving toughness cannot provide fundamental change of the physical properties of the ceramic; apparent toughness may be improved, but its value may be only one fifth of that of a metal. The method of confirming development of cracks by ultra-sonic waves may allow measurement on the test piece level; however, when it is to be applied to actual parts, it is accompanied by problems for use, such as problems of attaching the sensor to the ceramic parts or additional installation of measuring instruments. Reliability cannot be ensured for use of a ceramic by using the method which does not directly diagnose the state of the machine part.

SUMMARY OF THE INVENTION

An object of this invention is to provide a ceramic body which in use is subjected to stress and which is adapted to permit accurate monitoring of its condition.

A further object of the invention is to provide a method and apparatus for monitoring change in a sintered ceramic body.

Another object of the present invention is to provide method and apparatus for judging the service life or remaining useful life of a ceramic part, thus improving maintenance.

The invention is based on the concept of a diagnostic conductive element provided in or on the sintered ceramic of an actual machine part. The conductive element should intimately contact the ceramic.

In summary, the invention can provide a life diagnostic system to permit judging of the service life of a ceramic structural machine part and determining of maintenance requirement by measuring the change in resistance of the electrically conductive element which may be due to breaking, deformation, temperature, oxidization or corrosion thereof.

In one aspect, the invention provides a ceramic body which in use is subjected to stress and undergoes gradual change with time as a result of the stress. The ceramic body comprises a sintered ceramic material and an electrically conductive element in contact with this material. The element has a measurable electrical resistance which is increased irreversibly in dependence on the gradual change of the body. From the measured electrical resistance, there can be obtained information about the change of the ceramic body.

The electrically conductive element is suitably located at a region of said body which undergoes structural change as a result of said stress, and this structural change is typically formation of cracks.

The electrically conductive element preferably consists of material having a bulk electrical resistance of less than 1 $\Omega$.cm, and preferably the resistance is uniform along its length.

In one form of the invention, the electrically conductive element, as seen in cross-section, comprises a bundle of elongate members selected from fibers and whiskers. Whiskers are short fibers. The fibers or whiskers are gradually broken in use, giving a gradual increase in electrical resistance of the conductive element. Preferably, on average, as seen in cross-section, the electrically conductive element comprises at least ten of these elongate members, more preferably a number in the range 100 to $10^5$. The bundle of elongate members may be entirely made of conductive elongate members or may be a mixture of insulating and conductive fibers or a mixture of insulating and conductive whiskers. The bundle may comprise additionally electrically insulating particles and/or electrically conductive particles.

The electrically conductive element preferably has a diameter in the range 100 μm to 1 cm, more preferably 100 μm to 1 mm.

The electrically conductive element may be embedded in and co-sintered with said ceramic material, or may be formed on the surface of the ceramic material before or after its sintering.

The invention can be applied to a wide variety of ceramic parts, for example:

a) a gas turbine part selected from a moving blade, a stationary blade, a transition piece of a combustor, a heat exchanger part, a shroud part, and a duct part, b) a nuclear fission power plant part selected from a shielding material part, a heat exchanger part and a piping part, c) a nuclear fusion plant part which is installed on the side remote from the plasma of a wall of a vacuum containment vessel, d) a part of a magnetohydrodynamic power plant for generating electrical energy by movement of a high-temperature gas, said part comprising an inner wall part of a high-temperature gas exhaust duct, e) an automotive turbocharger rotor part, or f) a tundish of a metal casting machine.

The ceramic body of the invention may also be defined as a ceramic body which in use is subjected to stress and undergoes gradual change with time as a result of the stress, the ceramic body comprising sintered ceramic material and having an electrically conductive element at a region of the material which is structurally changed by the stress. The electrically conductive element comprises as seen in cross-section, at least 100 elongate members selected from fibers and whiskers.

In another aspect, the invention provides a method of detecting change of a ceramic sintered body caused by stress comprising sensing electrical resistance of a conductive element intimately contacting a sintered ceramic material of the body and assessing the change of said body from change of the sensed electrical resistance. The change of the ceramic sintered body is typically change of a mechanical property, e.g. strength. The step of assessing the change of the ceramic may be performed by comparing the sensed electrical resistance with at least one predetermined value thereof. The predetermined value of the electrical resistance of said electrically conductive element may be one or more of an initial value of said electrical resistance and a predetermined critical maximum value of said electrical resistance.

The invention further provides a method of determining a value of a remaining useful working lifetime of a ceramic body which in use is subjected to stress and undergoes gradual change caused by the stress, comprising the steps of sensing, after a period of time of use of the body, electrical resistance of an electrically conductive element contacting ceramic material of the body, and calculating the value of remaining useful working lifetime in dependence upon the sensed electrical resistance. The steps of calculating the value of remaining useful working lifetime may comprise comparing the sensed electrical resistance with a predetermined pattern of variation of the electrical resistance of said electrically conductive element in dependence upon said change of said body.

The method of use of the ceramic body of the invention may advantageously include relieving thermal stress in the body by heating the body by electrical resistance heating of the electrically conductive element.

In yet another aspect, the invention provides apparatus comprising a ceramic body and monitoring means therefor, the ceramic body comprising sintered ceramic material which in use of the body is subjected to stress, and an electrically conductive element contacting the ceramic material, the ceramic material undergoes gradual change as a result of said stress applied thereto in use. The electrically conductive element has a measurable electrical resistance which increases irreversibly in dependence on said change of ceramic material. The monitoring means comprises measuring means for measuring said electrical resistance. The monitoring means preferably comprises judging means for comparing an electrical resistance value measured by the measuring means with at least one predetermined electrical resistance value, and providing an output dependent upon a result of the comparison. The judging means may include comparison means for comparing the value of electrical resistance measured by said measuring means with the predetermined value and providing an output signal when the measured electrical resistance exceeds a predetermined threshold value. The monitoring means may further include means for calculating a value relating to a remaining useful working life of said ceramic body, on the basis of the measured electrical resistance. Suitably the monitoring means includes storage means for storing a predetermined pattern of change of the electrical resistance of the conductive element in dependence on change of said ceramic material, and the judging means includes comparison means for comparing the measured electrical resistance with the predetermined pattern.

In the present invention, the electrically conductive element in contact with the ceramic material may be composed of a material having a low electrical resistance such as C, SiC, TiN, TiC, ZrN and $Cr_2N$ and metals such as W, Mo, Ta and Nb. Especially it is effective to combine conductive fibers, whiskers and particles with heat-resistant insulating fibers, whiskers and particles. A combination of two or more types fibers and particles having different elasticity is also effective. It is of particular advantage that the electrically conductive element may also serve to reinforce the ceramic part. In addition to simple substances as C, SiC, etc., it is effective to use composite conductive materials such as C/SiC, $C/Al_2O_3$, $C/Si_3N_4$, $C/Si_2N_2O$, $SiC/Si_3N_4$, $SiC/Si_2N_2O$, $SiC/Al_2O_3$, $TiN/Al_2O_3$, $TiN/Si_3N_4$, and $TiN/Si_2N_2O$.

In the present invention, change in resistance of the electrically conductive element may be caused by the pulling out, breaking, interfacial contact, deformation, chemical corrosion or temperature change of the material, e.g. fibers of the conductive element. This change may be measured and compared with a threshold value, thereby permitting life prediction, life diagnosis and maintenance diagnosis. For example, cracks occurring in the ceramic will spread into the conductive element, resulting in increased resistance. This value is read and is compared with a threshold value, e.g. by a computer installed outside. If the threshold is exceeded, the stop signal may be issued automatically. This allows the equipment to be stopped, and faulty parts to be replaced, before the ceramic parts are broken.

The functional ceramic bodies of the invention can be applied to various types of machine structural parts. When the conductive circuit is installed on various types of machine structural parts, it need not be installed on the whole of such a part; it may be installed only close to the place subjected to the maximum stress or on a surface subjected to wear. Preferably, the element should be mounted close to the surface (5 mm or less from the surface). This is because the ceramic part tends to crack, resulting in linear fracture, so sensitivity to surface crack is very important. For example a crack occurring on the surface gradually cuts the bundle of fibers, resulting in increased resistance. The fibers in the bundle are gradually broken and the resistance is gradually increased by providing not a single fiber but a bundle of long fibers, a bundle of combination of fibers and particles.

In the present invention it is also possible to reduce the effect of external thermal stress by using the conductive element as a heater for the ceramic body, to relax thermal stress in the body.

The ceramic body can be manufactured by conventional processes such as pressure sintering, reaction sintering, HP (hot pressing) and HIP (hot isostatic pressing). It is possible to use a ceramic having a greater strength when the said ceramic is reinforced by making it complex or by particle dispersion.

The ceramic used may be a reaction sintered ceramic comprising one or more of oxide, carbide, nitride and carbonitride. This is because change in dimensions of the reaction sintered ceramic is as small as 1 percent or less when sintered from the molded body to the sintered body; so the electrically conductive circuit can be easily provided in or on the molded body without being deformed or broken, and residual stress does not remain in the conductive element itself. Furthermore, since reaction sintered ceramic is porous, it is possible to coat the surface or impregnate the interior with a substance which provides characteristics required when the body is used as a structural part. CVD (chemical vapor deposition), CVI (chemical vapor implantation), PVD (physical vapor deposition), ion implantation and laser methods are available for coating and impregnation. Thus, the surface of the reaction sintered ceramic provided with the conductive element can be composed of compact materials having excellent resistance against abrasion, heat and corrosion. Furthermore, a combined use with the HIP method makes it possible to compact the material after reaction sintering.

One form of reaction sintered ceramic body of the invention can be manufactured as follows: the conductive element comprises metallic powder (Si, Al, etc.) or metallic powder and inorganic compound (one or more of oxide, carbide, nitride or carbonitride) incorporated in or on the ceramic body, and the ceramic body is heated in an atmosphere of reactive gas comprising one or more of oxidizing, carbonizing, nitriding and oxynitriding gas. The metallic powder reacts with the reactive gas to generate the product; by combining the element with the said product, a reaction sintered ceramic can be provided with the conductive element having a porosity of 5 to 30 vol. percent.

The conductive element may have one-, two- and three-dimensional orientation.

Another manufacturing method for the ceramic body according to the present invention is the green sheet forming method, which is effective to reduce manufacturing cost. The green sheet is formed by a doctor blade, using a slurry comprising the organic binder and ceramic powder, and is cut by punching into a desired shape and sintered. The appropriate thickness of the green sheet is 1 to 5 mm, but depending on the form of the part, any desired thickness can be selected in the forming of the diagnostic conductive element. After the green sheets are stacked and sintered, finishing is done as required.

Connection between the conductive element in or on the ceramic and external wiring can be made for example by brazing, laser or ultra-sonic waves. Furthermore, use on the surface of a metallic wire such as steel, tungsten and platinum provides heat resistance.

The present invention can provide substantially improved reliability of ceramic parts, and facilitates their application to various types of plant components and machine parts, such as engine parts, by providing a system which judges the condition of the part under the actual operating conditions, and allows calculation of service life and aids maintenance.

BRIEF DESCRIPTION OF THE DRAWINGS

Embodiments of the invention will now be described by way of non-limitative example with reference to the accompanying drawings, in which:

FIG. 24 is an illustrative diagram of one form of diagnostic ceramic body of the invention;

FIG. 25 is a perspective partial view of one form of conductive element used in the invention;

FIG. 26 is an explanatory view of another form of conductive element used in the invention;

DESCRIPTION OF PREFERRED EMBODIMENTS

Figure 1:
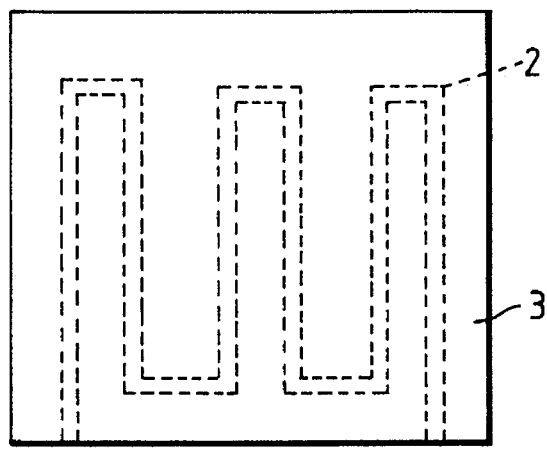
FIG. 1 is a plan view of a diagnostic ceramic body of the invention which is a first wall part of a nuclear fusion reactor.

In the drawings, parts having the same or similar functions in the various embodiments are given the same reference numbers.

In all of the following Embodiments, the electrical resistance of the conductive element used for life diagnosis is less than 1 Ω.cm.

EMBODIMENT 1

Figure 2:
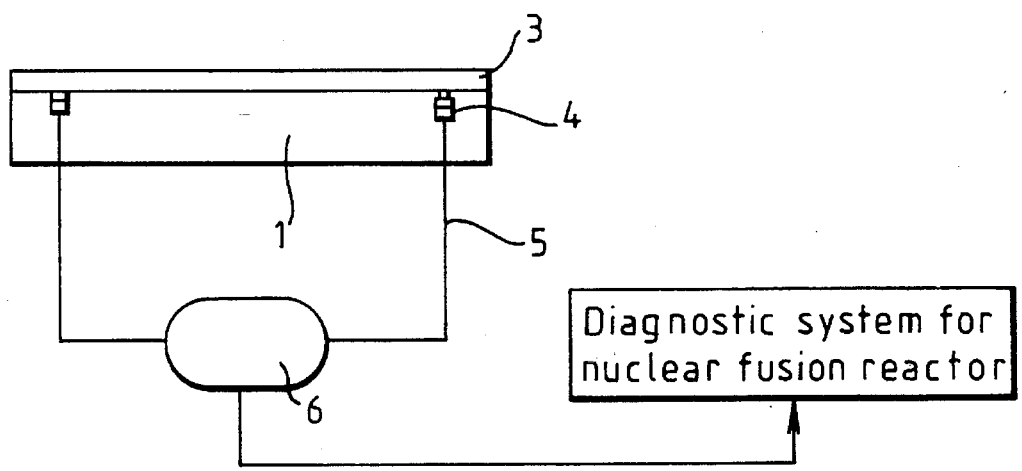
FIG. 2 is a diagram of an application of the first wall part of a nuclear fusion reactor shown in FIG. 1.

A study has been made on the first wall parts of a nuclear fusion reactor. Such a wall part is shown in FIG. 1 and FIG. 2. To make the ceramic parts constituting the first wall parts of the nuclear fusion reactor, 13 parts by weight of a mixture of polyethylene, stearic acid and synthetic wax is added to 100 parts by weight of metallic Si powder having an average particle diameter of 1 μm, and is kneaded. This material is made into a 2 mm thick, 100 mm square plate 1 by an extruding machine. A composite long fiber (1.5 mm in diameter) comprising carbon fibers (10 μm in diameter, 1000 μm in length) and $Al_2O_3$ fibers (5 μm in diameter, 1000 μm in length) is used as a conductive element 2 for life diagnosis on this plate. The mixing ratio of the carbon fiber and $Al_2O_3$ fiber used is 50 to 50 vol percent, but is not limited to this value; the carbon fiber to $Al_2O_3$ fiber ratio can for example be 30 to 70 or 80 to 20 vol %. The diameter of the element 2 should preferably be 0.1 mm or more.

The molded plate 1 is heated to 1350° C. in a furnace under nitrogen atmosphere at a temperature rise rate of 1° C./min, and held at 1350° C. for 1 hour, and cooled in the furnace to obtain a reaction sintered $Si_3N_4$ ceramic provided with the electrically conductive element 2 for life diagnosis. The binder is degreased in the temperature rise. A compact BN film 3 0.3 mm thick is formed on the surface of the reaction sintered ceramic 1 by plasma flame spraying to provide a heat resistant layer. Since the surface of the reaction sintered material is porous, BN is formed even in the pores; thus, the film 3 is strongly adhered. Terminals 4 of the element 2 are connected to copper wire 5 by silver brazing, and an external measuring device 6 is connected.

Figure 3:
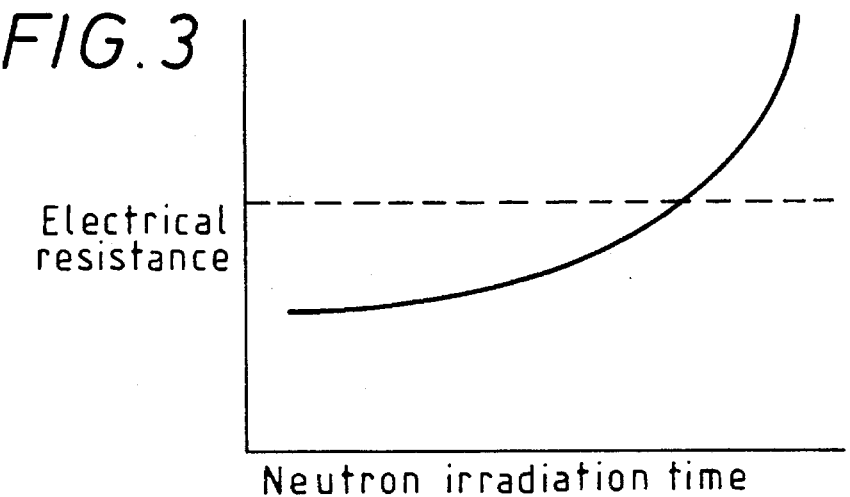
FIG. 3 is a graph representing the relationship between neutron irradiation time for the first wall part of a nuclear fusion reactor shown in FIG. 1 and resistance of the conductive element.

Such ceramic parts are used as the first wall parts of a nuclear fusion reactor. In use the BN film 3 is damaged by neutron irradiation and change in resistance of the element 2 is observed as shown in FIG. 3, demonstrating that the life diagnosis of the first wall parts of the nuclear fusion reactor is possible. This change in resistance may be fed to a nuclear power plant control system. When this resistance has exceeded a specified threshold, the plant may be automatically stopped to allow maintenance and inspection.

$Si_3N_4$, $Si_2N_2O$, AlN, $Al_2O_3$, $ZrO_2$, $B_4C$, BN and mullite powder and whiskers may be mixed with the Si powder used in Embodiment 1 to manufacture composite ceramics ($Si_3N_4/Si_3N_4$, $Si_3N_4/Si_2N_2O$, $Si_3N_4/AlN$, $Si_3N_4/Al_2O_3$, $Si_3N_4/ZrO_2$, $Si_3N_4/B_4C$, $Si_3N_4/BN$, $Si_3N_4$/mullite, $Si_3N_4/SiC$, etc.) which can be provided the conductive element for life diagnosis, by a reaction sintering method.

Ceramic molding is possible in many ways to meet the requirements of the various shapes of the parts of the present invention, such as the doctor blade method, powder molding, CIP, injection molding, cast molding, extrusion, etc.

The binders used for molding can be as generally used for molding ceramics, including high-molecular weight materials such as polyvinyl butyral and polyethylene, silicone series compound, and polysilane series compounds. Degreasing methods for these binders need not be specified here in particular; they can be degreased by controlling the temperature rise speed at the time of sintering.

EMBODIMENT 2

Using metallic Al powder in place of metallic Si powder in Embodiment 1, it is possible to make an AlN ceramic provided with a conductive element for life diagnosis by reaction sintering, and this may be used in the same way for the first wall parts of the nuclear fusion reactor.

EMBODIMENT 3

A further wall part for a nuclear fusion plant was made as follows. 13 parts of a mixture of polyethylene, stearic acid and synthetic wax is added to 97 parts by weight of SiC powder having an average particle diameter of 0.1 μm, 1 part by weight of BeO as sintering agent and 2 parts by weight of AlN, and the whole mixture is kneaded to produce a material, which is shaped into in a 2 mm-thick, 100 mm-square plate by an extruding machine. A composite long fiber (2.5 mm in diameter) comprising carbon fibers (100 μm in diameter, 1000 μm in length) and $Al_2O_3$ fibers (100 μm in diameter, 1000 μm in length) is formed to make a conductive element 2 for life diagnosis 2 (FIGS. 1 and 2) by molding on this plate. The mixing ratio between carbon and $Al_2O_3$ fibers used for the element 2 was 70 to 30 vol percent.

The molded plate 1 is heated at a temperature rise rate of 1° C./min. up to 2150° C. in a furnace in an atmosphere of argon, and held for three hours at 2150° C. It is then cooled in the furnace, to obtain an atmospheric pressure sintered SiC ceramic body 1 provided with the element 2. To provide heat resistance, a compact 0.3 mm-thick BN film 3 was formed on the surface carrying the element 2 by plasma spraying. Copper wiring 5 was silver-brazed on terminals 4 of the element 2 and was connected to external measuring instrument 6 it was then connected to a nuclear power plant diagnostic system.

EMBODIMENT 4

Figure 4:
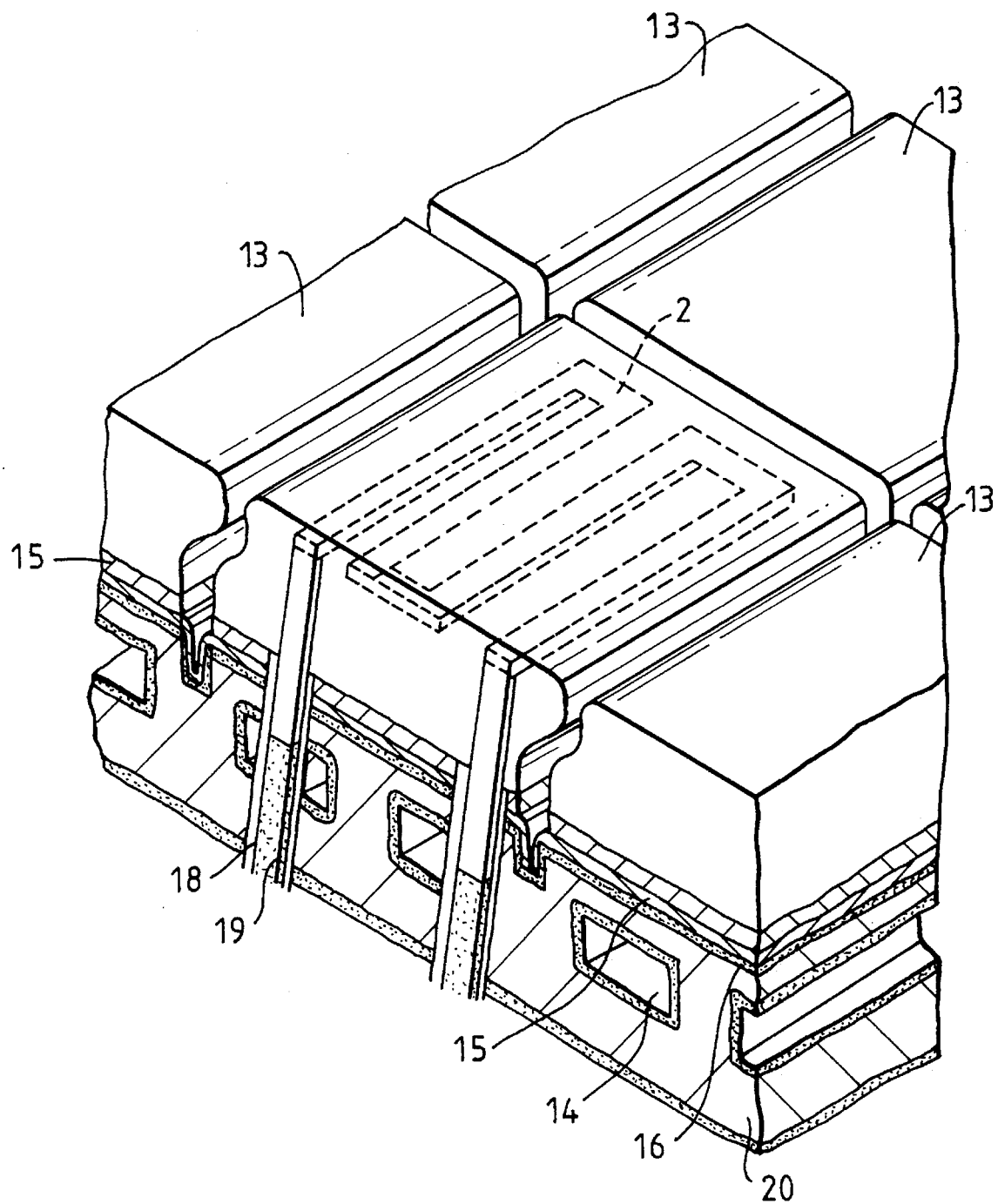
FIG. 4 is a partial perspective view of wall parts of a nuclear fusion reactor.

FIG. 4 shows the first wall of the nuclear fusion reactor, wherein reactor wall ceramic plates 13 are manufactured in the same way as the plates in Embodiment 3. Each ceramic plate 13 is silver-brazed to a substrate 20 of austenite series stainless steel via a graphite substrate 15 containing carbon fiber whose coefficient of thermal expansion is similar to that of the ceramic plate. A metallic coating layer 16 is present on the steel substrate 20. The substrate 20 is provided with cooling channel 14 in which water flows for cooling.

The element 2 is located inside the BN film which is on the outer surface of the plates 13. The element 2 is extended to the substrate 20 and is connected to the copper wire 19. $Al_2O_3$ protective pipes 18 cover the connections between the copper wire and element 2.

The BN film of the ceramic plates 13 is damaged by neutron irradiation and the change in resistance appearing in the element 2 is as illustrated in FIG. 3.

EMBODIMENT 5

Here the stationary blade part of a gas turbine in a thermal power plant system is studied. To manufacture the material for ceramic parts constituting the stationary blade parts for gas turbine, 108 parts by weight of the binder comprising 6 parts by weight of polyvinyl butyral, 24 parts by weight of trichloroethylene, 32 parts by weight of tetrachloroethylene, 44 parts by weight of n-butyl alcohol and 2 parts by weight of butylphthalyl glycolic acid is added to 100 parts by weight of metallic Si powder having an average particle diameter of 0.5 μm, and the mixture is kneaded by a ball mill for 24 hours, to make a slurry. The slurry is subjected to vacuum degassing to remove gas bubbles, and cast into a rubber mold for the stationary blade of the gas turbine by the mold casting method. Then it is dried for ten hours to make a molded body. In the molding, a composite fiber (3 mm in diameter), consisting of 70 vol % of carbon fiber (100 μm in diameter) and 30 vol % of SiC fiber (100 μm in diameter) is formed for a conductive element in the rubber mold according a specified pattern, and the slurry is cast around it.

This molded body is heated at a temperature rise rate of 1° C./min. up to 1350° C. in a furnace with a nitrogen atmosphere, and held at 1350° C. for 1 hour and then cooled in the furnace to obtain a reaction sintered $Si_3N_4$ ceramic body 1 (FIG. 5) provided an element 2 for life diagnosis 2. The binder is degreased during the temperature rise. To provide heat resistance, a 30 μm-thick compact $ZrO_2$ film is formed on the surface of the reaction sintered ceramic by plasma spraying. Tungsten wires 5 are brazed on terminals of the element 2, and connected to an external measuring instrument 6, which is connected to a thermal power plant diagnostic system.

Figure 6:
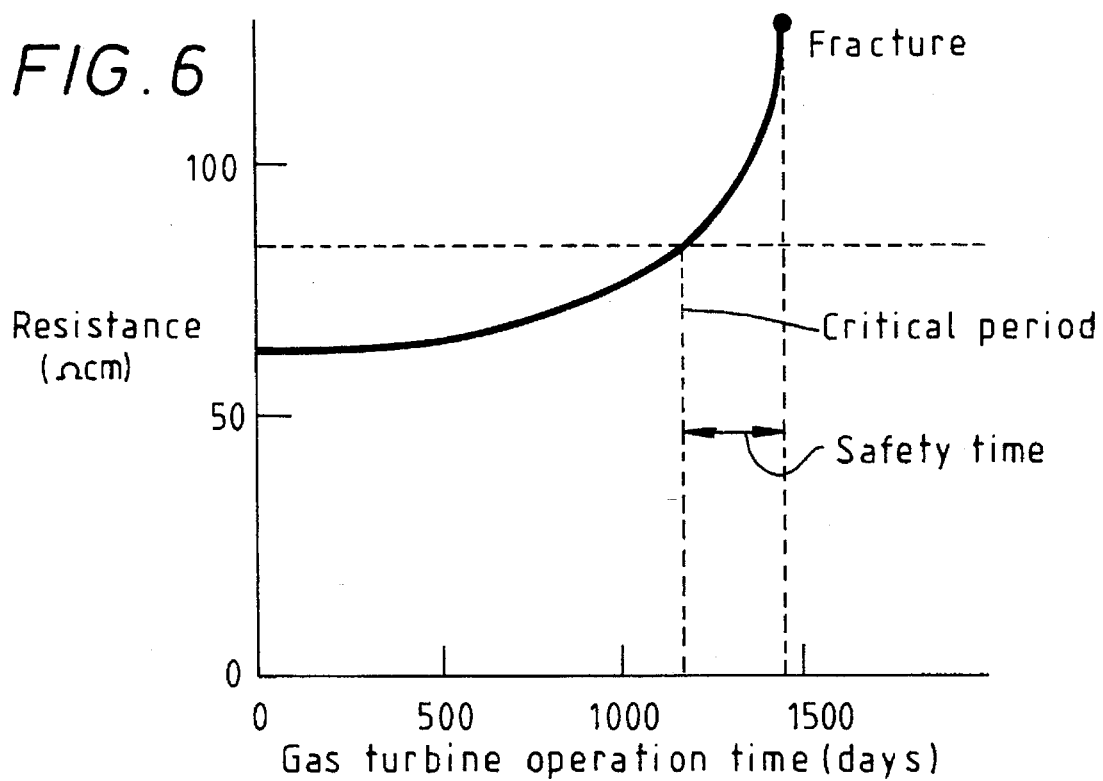
FIG. 6 is a graph representing the relationship between gas turbine operation time and resistance of the conductive element of the ceramic body of FIG. 5.

In use of this stationary blade part of a gas turbine, the element 2 becomes increased in resistance, typically as shown in FIG. 6, revealing that the life diagnosis was possible. This diagnosis provides substantially improved reliability of the ceramic parts. The change in resistance may be fed to the thermal power plant diagnostic system, which issues a shut down signal if the resistance value has exceeded a specified threshold value, allowing maintenance and inspection.

FIG. 6 shows how the resistance varies with time of operation. The initial state of the ceramics is maintained for about 500 hours. After that the ceramic becomes damaged as cracks are generated due to stress, and these cracks progress into the interior of the ceramic body due to fatigue. The element 2 becomes thinner, due to this cracking, and its resistance increases gradually and irreversibly. FIG. 6 shows a critical use period at which the apparatus is stopped, before the ceramic body is destroyed. When the resistance change pattern of FIG. 6 is known, it is possible to determine the critical resistance level related to the desired critical period. This critical period is determined according to the size of the ceramic component, the position of the diagnosis element, the resistance of the diagnosis element and the safety coefficient.

Further, as the increase in the resistance is predictable, it is possible to lengthen the allowed residual life.

To make the film providing a compact dense surface of the reaction sintered ceramic, the surface layer may be a single layer or multi-layer film of SiC, BN, TiN, $ZrO_2$, diamond, $ZrB_2$ or the like, depending on the conditions and purpose of use.

EMBODIMENT 6

Using metallic Al powder in place of metallic Si powder in Embodiment 5, there is made an AlN ceramic blade part provided with a conductive element for life diagnosis by the reaction sintering method, and this is applied to a stationary blade part for a gas turbine. The sintering process involves heating at 1° C./min to 1400° C. and holding at 1400° C. in a nitrogen atmosphere. The pattern of change in resistance shown in FIG. 6 was observed in operation before the ceramic part was damaged.

Furthermore, $Si_3N_4$, $Si_2N_2O$, AlN, $Al_2O_3$, $ZrO_2$, $B_4C$, BN and mullite powder and whiskers may be mixed with the the Al powder to manufacture composite ceramics (AlN/$Si_3N_4$, AlN/$Si_2N_2O$, AlN/AlN, AlN/$Al_2O_3$, AlN/$ZrO_2$, AlN/$B_4C$, AlN/BN, AlN/mullite, AlN/SiC, etc.) provided with electrically conductive elements for life diagnosis, by the reaction sintering method.

EMBODIMENT 7

To make a moving blade part (of FIG. 7) of a gas turbine in a thermal power plant system, 108 parts by weight of a binder comprising 6 parts by weight of polyvinyl butyral, 24 parts by weight of trichloroethylene, 32 parts by weight of tetrachloroethylene, 44 parts by weight of n-butyl alcohol and 2 parts by weight of butylphthalyl glycolic acid is added to 96 parts by weight of SiC powder having an average particle diameter of 0.5 μm and 4 parts by weight of BeO powder having an average particle diameter of 0.2 μm. The mixture is kneaded in a ball mill for 24 hours, to be made into slurry. The slurry is subjected to vacuum degassing to remove gas bubbles, and is cast into a rubber mold for the moving blade of the gas turbine, by the mold casting method. Then it is dried for ten hours to give a molded body. A composite conductive fiber 3 mm in diameter is formed from 80 vol % carbon fibers 6 μm in diameter and 20 vol % SiC fibers 10 μm in diameter, to form an electrically conductive diagnosis element, and arranged in the rubber mold according a specified pattern, and the slurry is cast around it.

Figure 7:
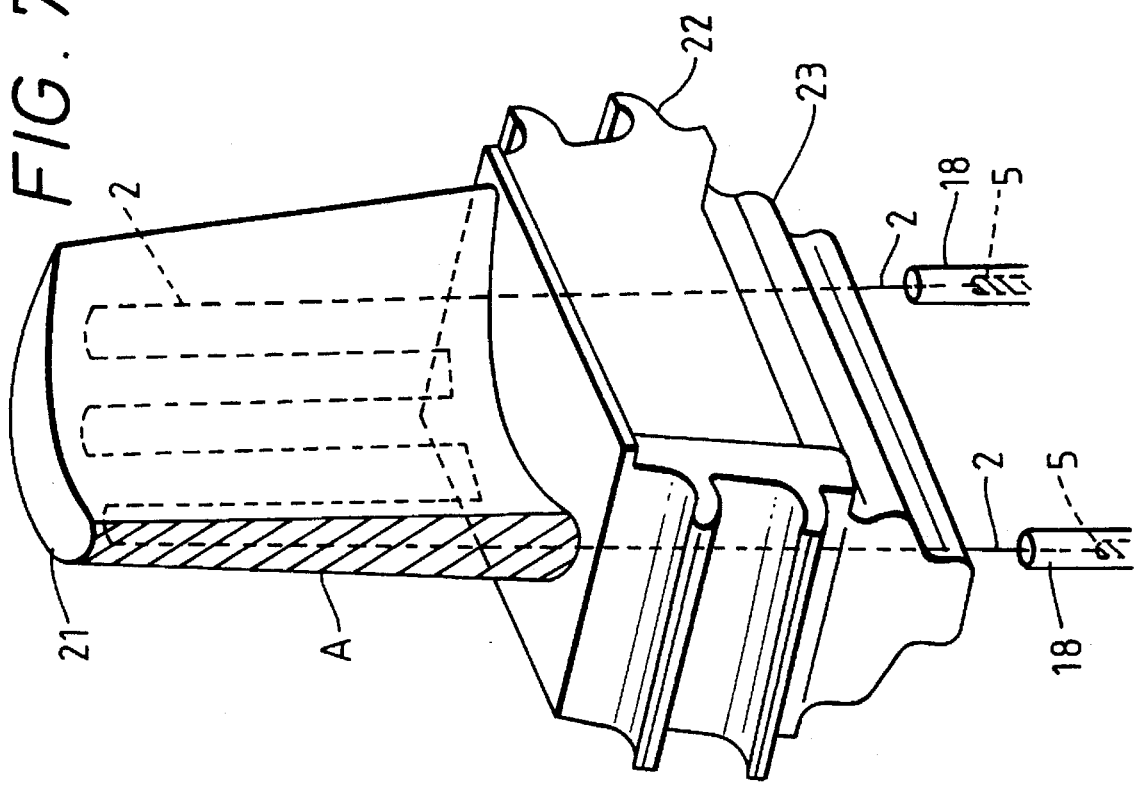
FIG. 7 is a perspective view of a gas turbine blade embodying the invention.

The molded body is heated at a temperature rise rate of 5° C./min. up to 2250° C. in a furnace of argon atmosphere, held for one hour at 2250° C. and then cooled in the furnace to obtain the SiC ceramic blade part (FIG. 7) provided with the element 2 for life diagnosis. The binder is degreased during the temperature rise. To provide heat resistance, a compact μm-thick $ZrO_2$ film is formed on the surface of the ceramic by plasma spraying. Tungsten wires 5 in insulating sleeves 18 are brazed on the terminals of the element 2 which extends to the turbine disk, and are connected to an external resistance measuring instrument. This is connected to the thermal power plant control system. This element 2 is used in the way already discussed, and demonstrates that the life diagnosis is possible. FIG. 7 shows the blade 21, dovetail 22 and insertion section 23.

The element 2 need not be installed over the whole of the machine structural part; it may be installed only close to the place A subjected to the maximum stress. Furthermore, the element should be mounted close to the surface (5 mm or less from the surface). This is because the ceramic parts tend to crack, resulting in linear fracture, so sensitivity to surface crack is very important. A crack occurring on the surface gradually cuts the bundle of fibers, resulting in increased resistance.

EMBODIMENT 8

To manufacture a shroud part 30 (FIG. 8) of a gas turbine, 108 parts by weight of a binder comprising 6 parts by weight of polyvinyl butyral, 24 parts by weight of trichloroethylene, 32 parts by weight of tetrachloroethylene, 44 parts by weight of n-butyl alcohol and 2 parts by weight of butylphthalyl glycolic acid is added to 95 parts by weight of $Si_3N_4$ powder having an average particle diameter of 0.1 µm, 3 parts by weight of sintering agent $Y_2O_3$ and 2 parts by weight of AlN, and the mixture is kneaded by a ball mill for 24 hours, to be made into slurry. The slurry is subjected to vacuum degassing to remove gas bubbles, and is cast into a rubber mold for the shroud segment part for a gas turbine. Then it is dried for ten hours, to give a molded body. A composite $C/Al_2O_3$ fiber (2 mm in diameter) of C fibers 6 µm in diameter and $Al_2O_3$ fibers 10 µm in diameter is arranged as a conductive element for life diagnosis in the rubber mold, according to a specified pattern, and the slurry is cast around it.

The molded body was heated at the temperature rise rate of 5° C./min. up to 1750° C. in a furnace of nitrogen atmosphere and was held for three hours. It was then cooled in the furnace to obtain an atmospheric pressure sintered $Si_3N_4$ ceramic shroud part (FIG. 8) provided with an element 2 for life diagnosis 2. The binder can be degreased during the process of temperature rise. To provide heat resistance, a compact 10 µm-thick $ZrO_2$ film is formed on the surface of the $Si_3N_4$ ceramic by plasma spraying. Copper wires 5 are silver-brazed on the terminals of the element 2 which extends to the exterior of the turbine casing, and is connected to an external resistance measuring instrument 6, which is connected to the thermal power plant control system. The element 2 and copper wire are insulated by the alumina protective tubes 18.

Figure 5:
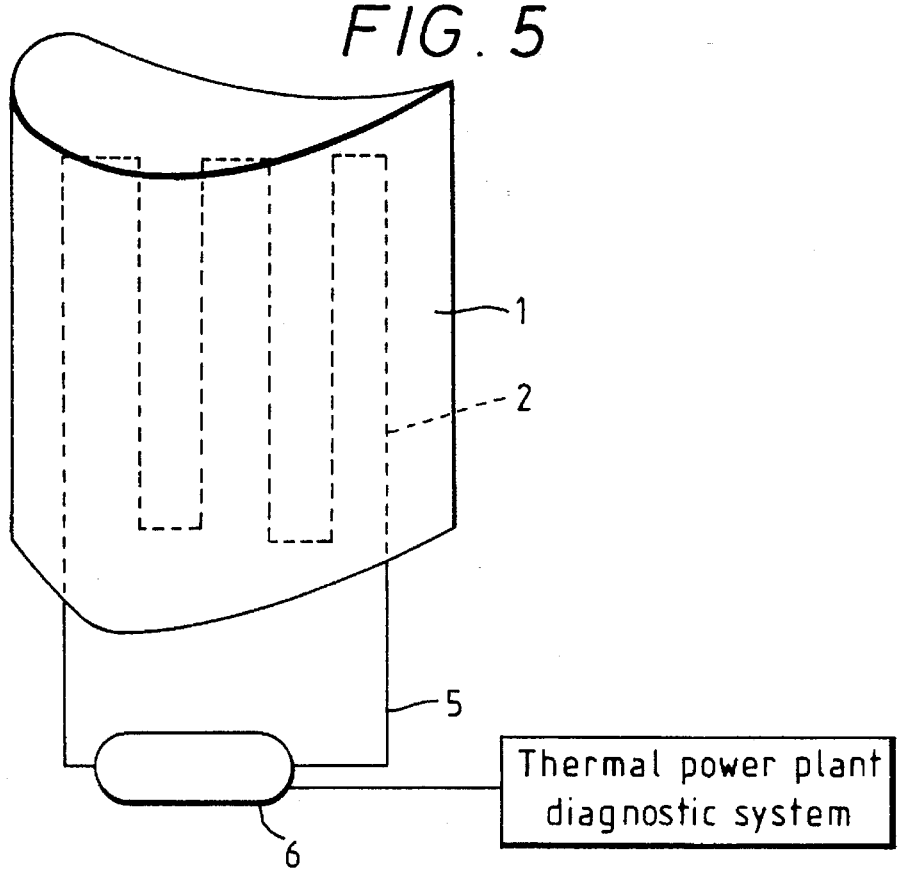
FIG. 5 is a diagram of a diagnostic ceramic body of the invention which is a gas turbine stationary part.
Figure 8:
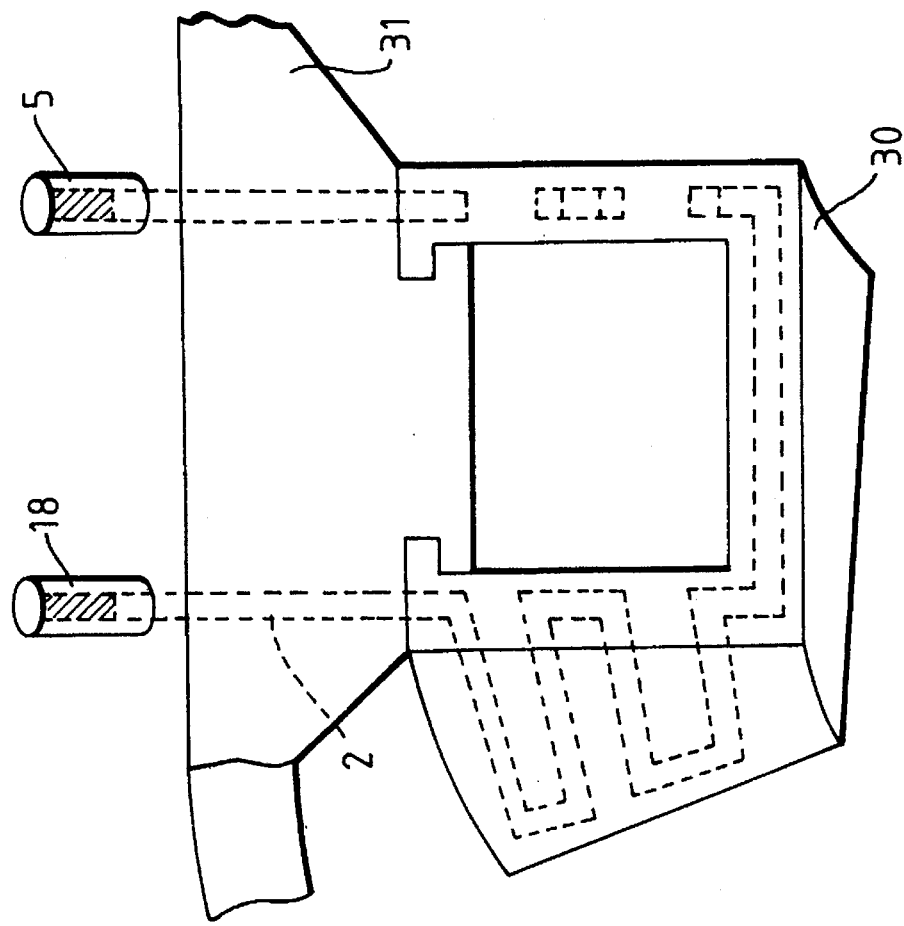
FIG. 8 is a perspective view of a gas turbine shroud part embodying the invention.

Ceramic parts as shown in FIG. 8 are applied as the shroud parts of the gas turbine, and a pattern of change in resistance in use as shown in FIG. 5 was observed before the ceramic parts were damaged.

Figure 9:
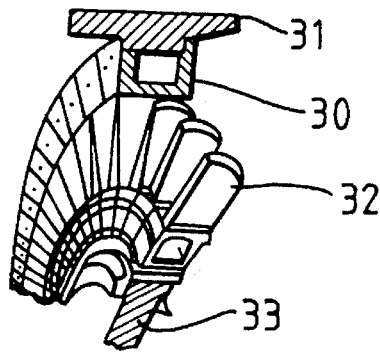
FIG. 9 is a partial perspective view of a gas turbine rotor.

FIG. 9 shows a rotary portion of a gas turbine with the built-in ceramic shroud part 30, casing 31, moving blade 32 and turbine disk 33.

EMBODIMENT 9

To manufacture another stationary blade part of a gas turbine, similar in shape to that of FIG. 5, 108 parts by weight of a binder comprising 6 parts by weight of polyvinyl butyral, 24 parts by weight of trichloroethylene, 32 parts by weight of tetrachloroethylene, 44 parts by weight of n-butyl alcohol and 2 parts by weight of butylphthalyl glycolic acid is added to 95 parts by weight of $Si_3N_4$ powder having an average particle diameter of 0.1 µm, 3 parts by weight of sintering agent $Y_2O_3$ and 2 parts by weight of AlN, and the whole mixture is kneaded by the ball mill for 24 hours, to be made into slurry. The slurry is subjected to vacuum degassing to remove gas bubbles, and is cast into a rubber mold for the stationary blade part of the gas turbine, according to the mold casting method. Then it is dried for ten hours, to make a molded body. A composite $SiC/Al_2O_3$ fiber (2 mm in diameter) consisting of 70 vol % SiC fiber (50 µm in diameter) and 30 vol % $Al_2O_3$ fiber (70 µm in diameter) is installed to make a conductive element for life diagnosis in the rubber mold according to a specified pattern, and the slurry is cast around it.

The molded body is heated at a temperature rise rate of 5° C./min. up to 1750° C. in a furnace in a nitrogen atmosphere and is held at 1750° C. for three hours. It is then cooled in the furnace, to obtain an atmospheric pressure sintered $Si_3N_4$ ceramic including a conductive element whose resistance can be measured. The binder is degreased during the process of temperature rise. To provide heat resistance, a compact 10 µ-thick $ZrO_2$ film is formed on the surface of the sintered $Si_3N_4$ ceramic by plasma spraying. Copper wire is silver-brazed on the terminals of the conductive element to connect it to an external resistance measuring instrument 6. This is connected to the thermal power plant diagnostic system.

Change in resistance in use as shown in FIG. 6 is observed before the ceramic part is damaged.

EMBODIMENT 10

To manufacture a ceramic corrosion-resistant piping part 17 (FIG. 10) of a thermal power plant, 108 parts by weight of a binder comprising 6 parts by weight of polyvinyl butyral, 24 parts by weight of trichloroethylene, 32 parts by weight of tetrachloroethylene, 44 parts by weight of n-butyl alcohol and 2 parts by weight of butylphthalyl glycolic acid is added to 97 parts by weight of SiC powder having an average particle diameter of 0.1 µm, 1 part by weight of sintering agent BeO and 2 parts by weight of AlN. This mixture is kneaded by a ball mill for 24 hours, to be made into slurry. The slurry is subjected to vacuum degassing to remove gas bubbles, and is cast into a porous mold (of plaster) to make the 10 mm-thick pipe having a diameter of 150 mm, using a centrifugal molding machine. A composite fiber (3 mm in diameter) consisting of 50 vol percent of carbon fiber (60 µm in diameter) and 50 vol percent of $Al_2O_3$ fiber (100 µm in diameter) is formed to make a conductive element for life diagnosis on the porous mold surface according to a specified pattern, and the slurry is cast around it. After wax is removed from inside the molded body, the body is treated at the temperature of 2100° C. in an atmosphere of argon for three hours. This causes the conductive element 2 for life diagnosis to be installed in the pipe part 17.

Figure 11:
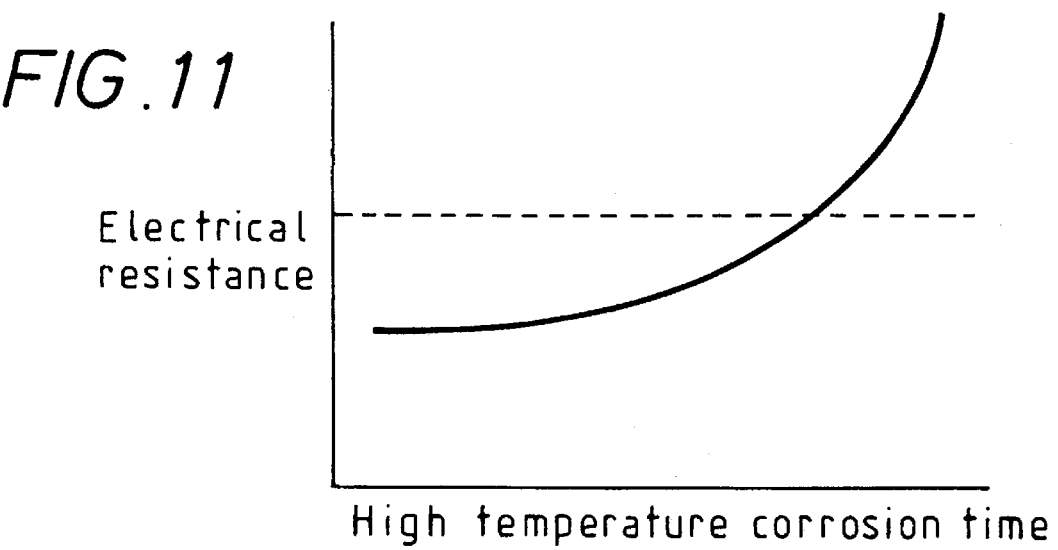
FIG. 11 is a graph representing the relationship between high temperature corrosion time and resistance of the conductive element of the piping part of FIG. 10.

Such ceramic parts 17 are applied as the corrosion-resistant piping parts of the thermal power plant, with the result that patterns of change in resistance shown in FIG. 11 are observed before the ceramic parts were severely damaged by corrosion. This shows that the life diagnosis is possible in such a case. This diagnosis provides substantially improved reliability of the ceramic parts.

EMBODIMENT 11

Figure 12:
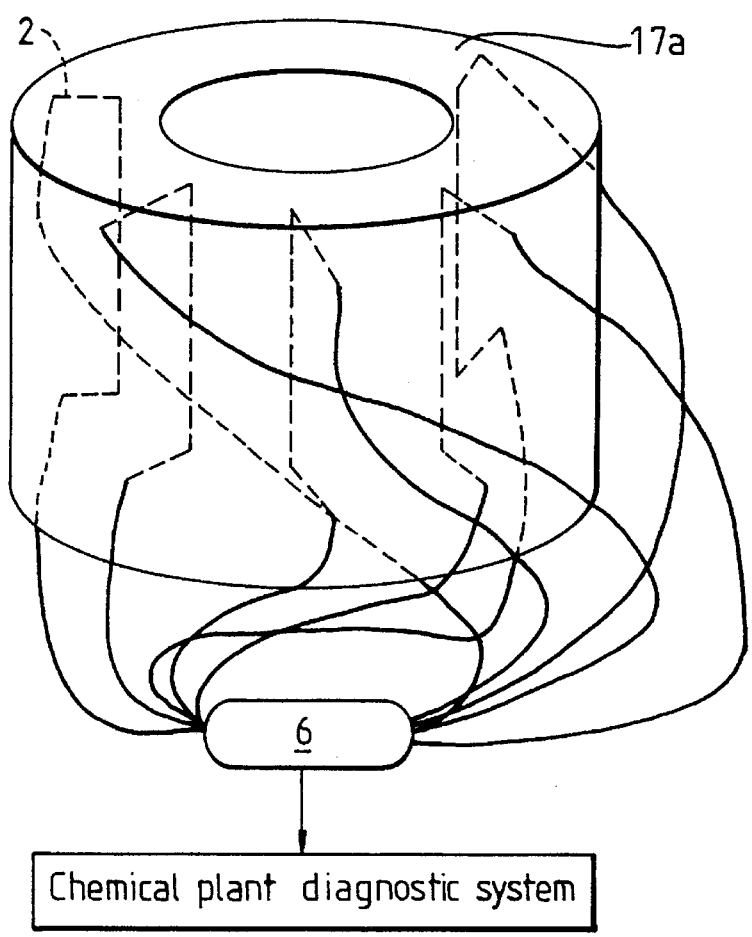
FIG. 12 is a diagram of a diagnostic ceramic system of the invention including another corrosion-proof piping part.
Figure 13:
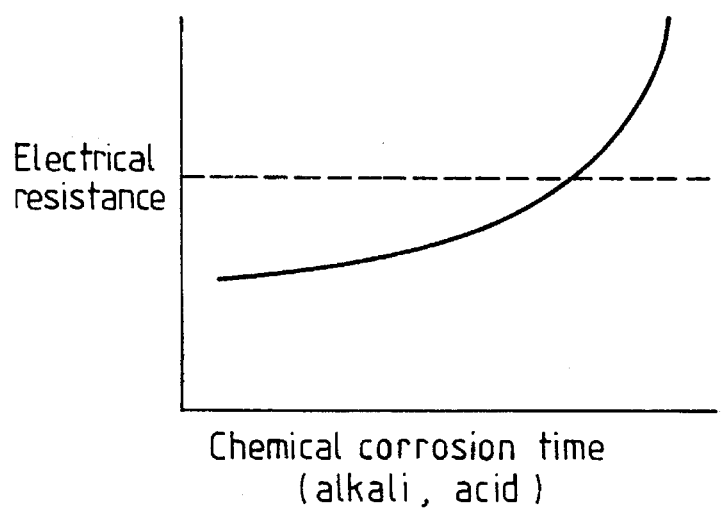
FIG. 13 is a graph representing the relationship between chemical (acid, alkali) corrosion time and resistance of the conductive element of the piping part of FIG. 12.

Piping parts as shown in FIG. 12 are made by a process similar to that of Embodiment 10, but with a plurality of individual conductive elements 2 embedded in the ceramic body 17a, as shown in FIG. 12 and all connected to resistance measuring device 6 which measures their electrical resistances sequentially. In a chemical plant, such piping parts may be subjected to corrosion by acid or alkali, which causes gradual irreversible change as shown in FIG. 13 in the electrical resistance of the elements 2, to allow life-time diagnosis. The several elements 2 also allow the location of a corrosion-affected region to be determined.

Figure 14A:
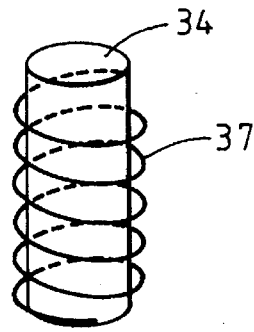
FIGS. 14(a) and 14(b) illustrate steps of a process of installation of the conductive element for a cylindrical part of the invention.
Figure 14B:
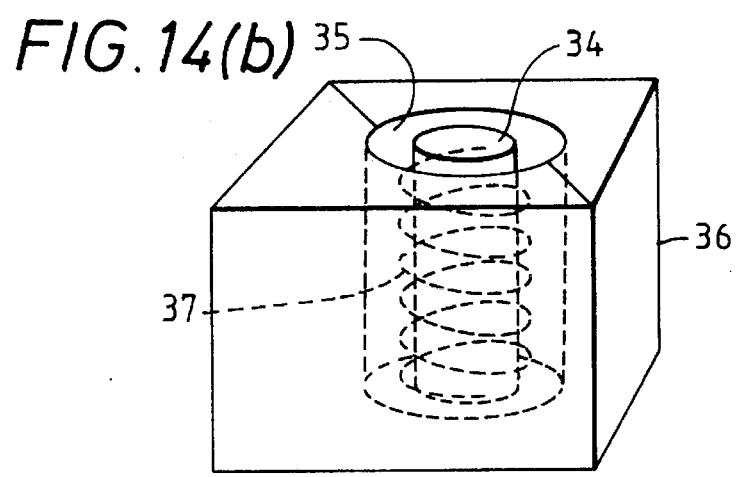
Figure 15A:
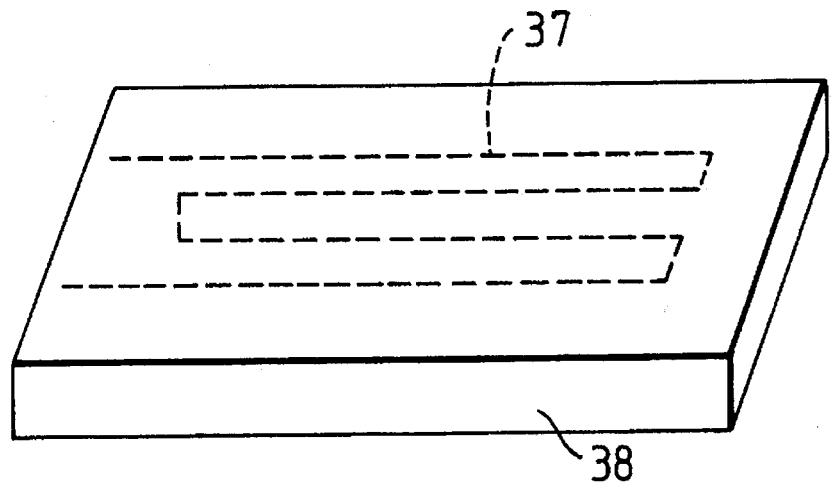
FIGS. 15(a), 15(b) and 15(c) illustrate steps of a process of making a tubular ceramic part of the invention.
Figure 15B:
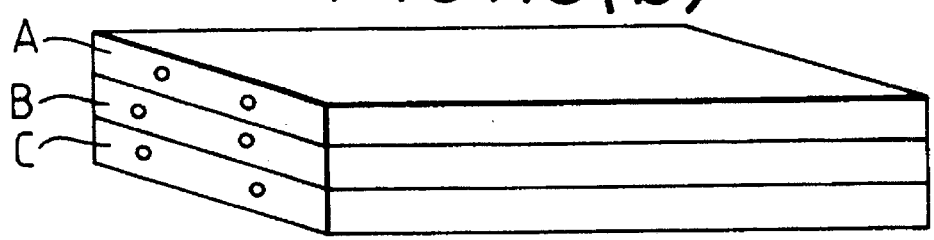
Figure 15C:
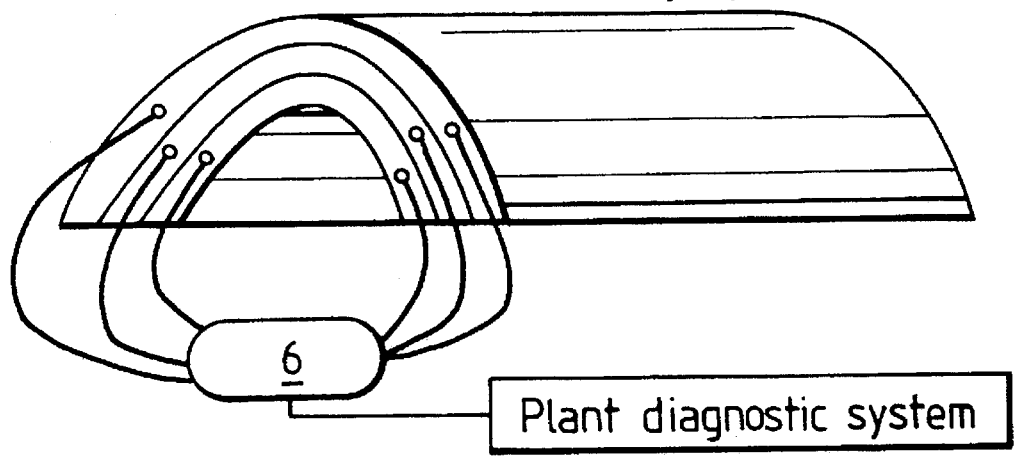
Figure 16A:
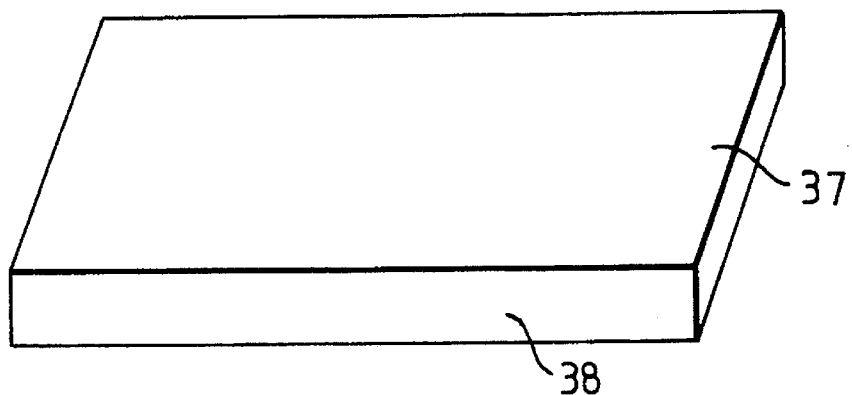
FIGS. 16(a), 16(b) and 16(c) are also process steps in the manufacture of a tubular ceramic part of the invention.
Figure 16B:
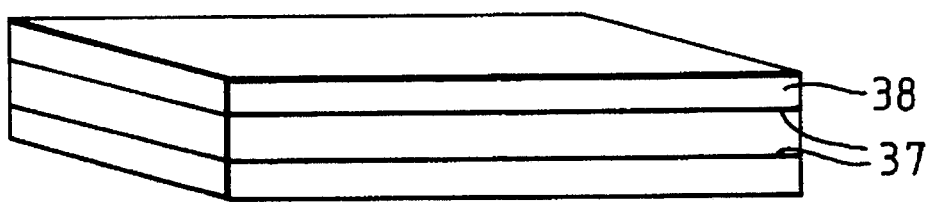
Figure 16C:
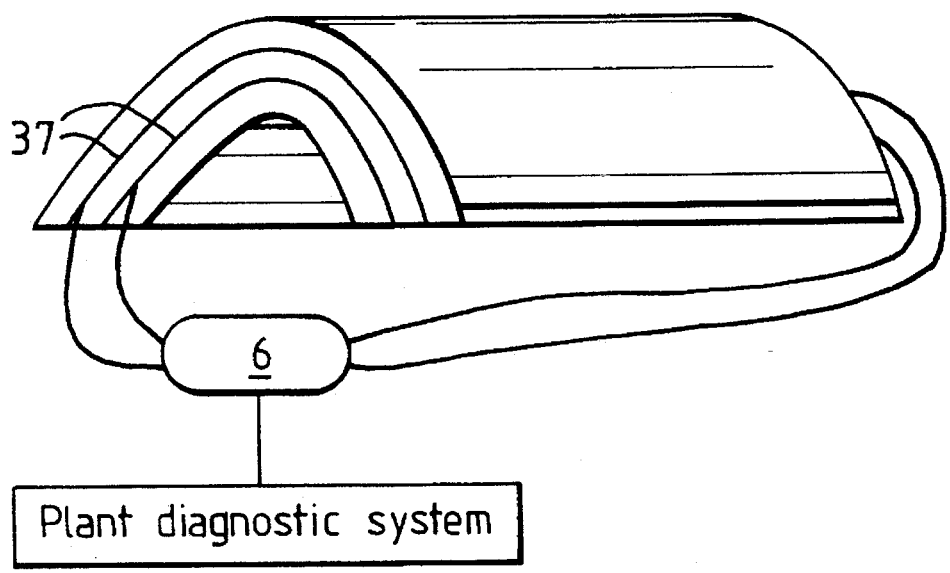

The methods shown in FIGS. 14, 15 and 16 can alternatively be employed to provide cylindrical parts having the conductive elements for life diagnosis. In FIG. 14(a) conductive element 37 comprising fibers such as carbon fibers is wound around a mandrel 34 and is heated. These parts are then placed in the mold 36 having a cavity 35 of the same shape as the desired part, and the ceramic slurry is cast, with the result that the element whose resistance is measured is formed (FIG. 14(b)).

FIG. 15 shows a method of molding into a part-cylindrical shape and sintering, including placing a conductive element 37 of fiber such as carbon fiber in or on a green ceramic sheet, and laminating a plurality of such green sheets thereon. This method allows installation of any desired measuring circuit between the inner and outer surfaces of the body.

FIG. 16 shows a method of molding into a part-cylindrical shape and sintering, including coating a conductive film 37 on the surface of two of the ceramic green sheets 38 and laminating the green sheets.

EMBODIMENT 12

Figure 10:
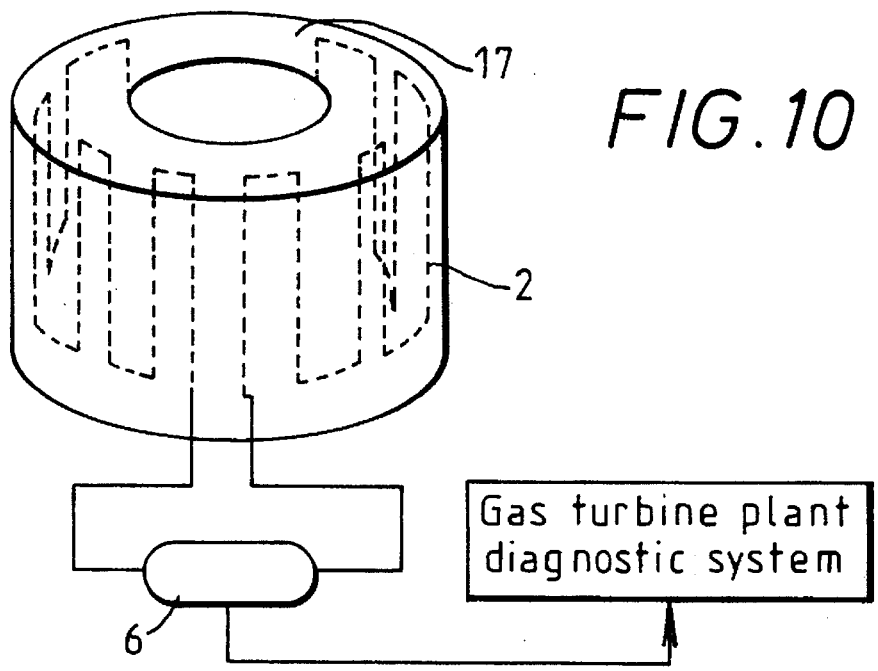
FIG. 10 is a diagram of a diagnostic ceramic system of the invention including a corrosion-proof piping part.

To manufacture another corrosion-resistant piping part embodying the invention, 108 parts by weight of a binder comprising 6 parts by weight of polyvinyl butyral, 24 parts by weight of trichloroethylene, 32 parts by weight of tetrachloroethylene, 44 parts by weight of n-butyl alcohol and 2 parts by weight of butylphthalyl glycolic acid is added to 100 parts by weight of Si powder having an average particle diameter of 0.1 μm, and the mixture is kneaded by a ball mill for 24 hours, to make a slurry. The slurry is subjected to vacuum degassing to remove gas bubbles, and is cast into a porous mold (plaster) to shape a 10 mm-thick pipe having a diameter of 150 mm, using a centrifugal molding machine. A composite fiber (3 mm in diameter) consisting of 50 vol percent of carbon fibers 100 μm in diameter and 50 vol percent of $Al_2O_3$ fibers 100 μm in diameter is arranged on the porous mold surface in a specified pattern, and the slurry is cast around it. After the wax is removed from the molded body by heating, it is treated at 2100° C. in a nitrogen atmosphere for three hours. In this way the conductive element whose resistance is measured for life diagnosis is installed in the pipe (as shown in FIG. 10).

When used as a corrosion-resistant piping part, this pipe shows the change in resistance pattern of FIG. 11 before the ceramic part is damaged by corrosion. This enables prediction at any time of the remaining useful life, i.e. life diagnosis.

Metallic aluminum powder may be used in place of the metallic Si powder to manufacture a AlN ceramic piping part of the same shape and the same behaviour of its conductive element.

EMBODIMENT 13

To manufacture an inner lining part of a gas turbine combustor, 13 parts by weight of a mixture of polyethylene, stearic acid and synthetic wax is added to 100 parts by weight of metallic Si powder having an average particle diameter of 1 μm, and the whole mixture is kneaded. It is then made into a 10 mm-thick, 100 mm-square plate by an extruding machine. A composite long fiber (1.5 mm in diameter) comprising carbon fibers (10 μm in diameter, 1000 μm in length), $Al_2O_3$ fibers (5 μm in diameter, 1000 μm in length) and SiC fibers (10 μm in diameter, 100 μm in length) is formed as a conductive element by molding on this plate. The mixing ratio of the carbon, $Al_2O_3$ and SiC fibers is 30 to 50 to 20 vol percent.

The molded body with the composite fiber is heated at a temperature rise rate of 1° C./min. up to 1350° C. in the furnace in a nitrogen atmosphere held for 1 hour at 1350° C. and cooled in the furnace to obtain a reaction sintered $Si_3N_4$ ceramic provided with the composite fiber as a conductive element for life diagnosis. The binder is degreased during the temperature rise. To provide heat resistance, a compact 0.3 mm-thick $ZrO_2$ film is formed on the surface of the ceramic. Since the surface of the reaction sintered material is porous, this film is strongly adhered. Copper wire is then brazed on terminals of the conductive element, and connected to an external resistance measuring instrument.

This ceramic part is used in the inner lining of the gas turbine combustor, with the result that the change in resistance of the conductive element shows a similar pattern to that of FIG. 6, while at the same time $ZrO_2$ film was damaged by the combustion in the combustion test.

EMBODIMENT 14

Metallic aluminum powder is used in place of the metallic Si powder in Embodiment 13 to manufacture an AlN ceramic part having the composite fiber as a conductive element for life diagnosis, by the reaction sintering method. This part is used in the inner lining of a gas turbine combustor, and gave a result similar to that shown in FIG. 6.

Figure 18:
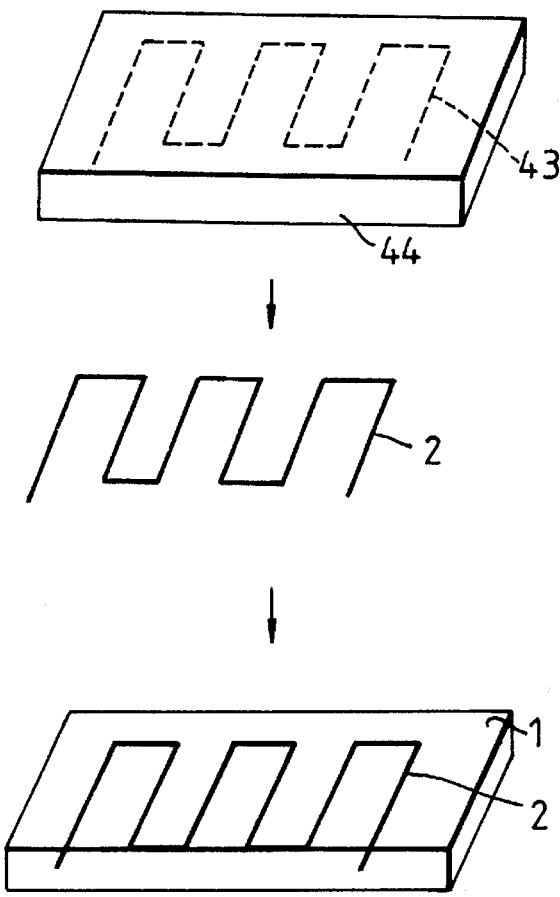
FIG. 18 illustrates process steps in another method of installation of the electrically conductive element in a ceramic body of the invention.

Various methods can be employed to form the conductive element whose resistance changes. A slurry comprising fiber as carbon fiber and a carrier medium may be cast into a mold having the desired shape of the element. FIG. 18 shows a mold 44 with a groove 43 of the desired shape. After being heated, the element 2 is taken out of the mold and is sintered integrally with the ceramic molded body 1, as shown in FIG. 18.

Figure 17:
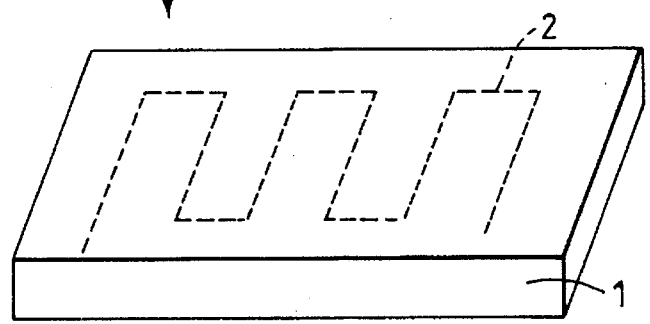
FIG. 17 is a diagram showing another process of installation of the electrically conductive element in a ceramic body of the invention.

Alternatively the slurry comprising the fiber as carbon fiber and the medium is printed into the desired pattern on the surface of the ceramic molded body, and is then sintered integrally with the molded body. The slurry may be made into the desired pattern by applying it from a nozzle 42 as shown in FIG. 17. After being heated, the element is sintered integrally with the ceramic molded body.

EMBODIMENT 15

To manufacture another part for the inner lining of a gas combustor, 13 parts by weight of a mixture of polyethylene, stearic acid and synthetic wax is added to 97 parts by weight of metallic Si powder having an average particle diameter of 0.1 μm, 1 part by weight of sintering agent BeO and 2 parts by weight of AlN, and the whole mixture is kneaded. It is then made into 15 mm-thick, 100 mm-square plates by an extruding machine. Composite long fibers (2.0 mm in diameter) comprising carbon fibers (100 μm in diameter, 10 μm in length) and $Al_2O_3$ fibers (100 μm in diameter, 1000 μm in length) are formed as five separate conductive elements 2 for life diagnosis (FIG. 19) by molding between two such plates. The mixing ratio between the carbon and $Al_2O_3$ fibers is 60 to 40 vol percent. To detect wear depth in combustion, the depth of the elements 2 from the surface film 3 described below is varied, as shown in FIG. 19.

The molded body is then heated at a temperature rise rate of 1° C./min. up to 2150° C. in a furnace of argon atmosphere and is held for three hours at 2150° C. Then it is cooled in the furnace to obtain the atmospheric pressure sintered SiC ceramic body 1 provided with five conductive elements 2 for life diagnosis. The binder is degreased during the temperature rise. To provide heat resistance, a compact 10 μm-thick $Al_2O_3$ surface film 3 is formed on the surface of the ceramic body by plasma spraying. Copper wire is then brazed on the terminals of the elements 2, and connected to an external resistance measuring instrument 6. This in turn is connected as illustrated to a thermal power plant diagnostic system.

Figure 19:
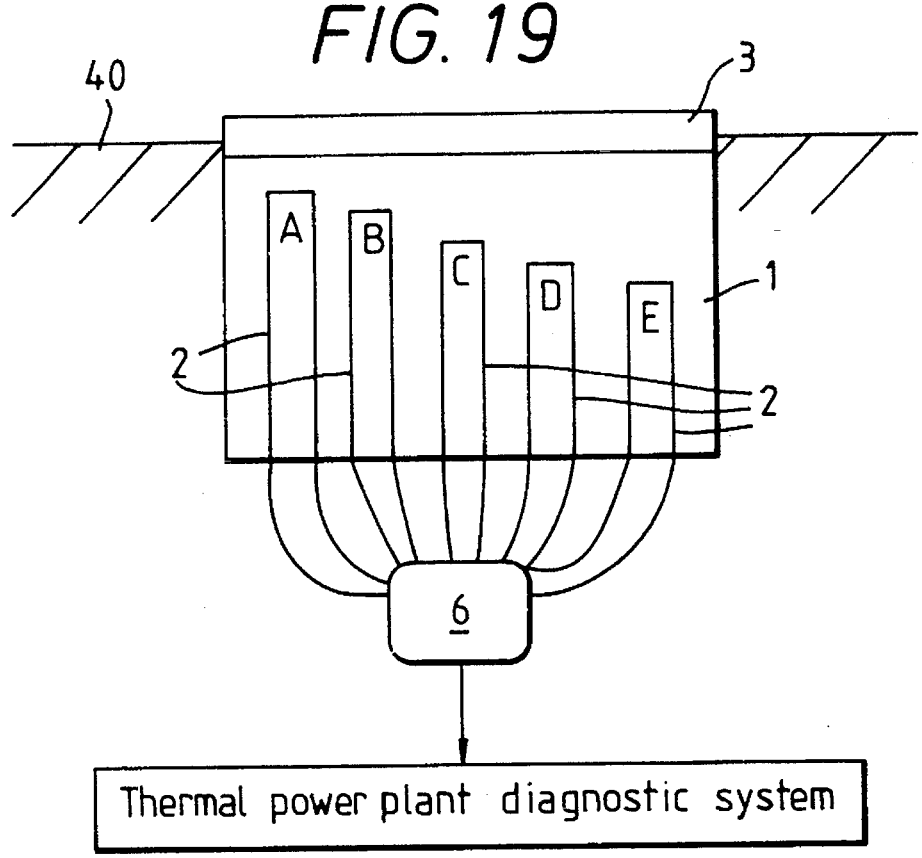
FIG. 19 is a diagram of a diagnostic ceramic system of the invention employing a combustor tile.
Figure 20:
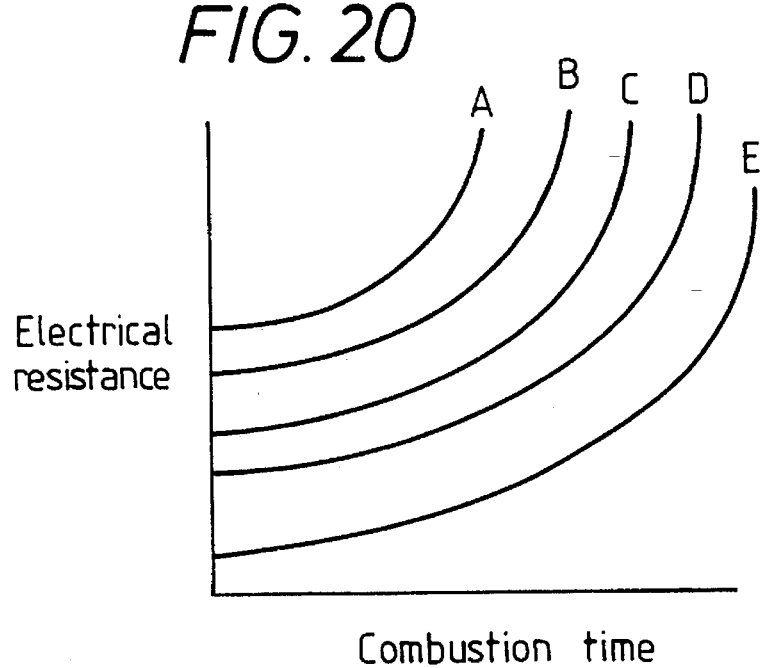
FIG. 20 is a graph representing the relationship between combustor operation time and resistance of the conductive elements in the tile of FIG. 19.

This ceramic part is used as illustrated in FIG. 19 in the inner lining 40 of a gas turbine combustor, with the result that patterns of change in resistance shown in FIG. 20 are observed when the wear proceeds and the $Al_2O_3$ film 3 is damaged. This shows that such a ceramic part provides information about wear and the life of the inner lining of the combustor.

EMBODIMENT 16

Figure 21:
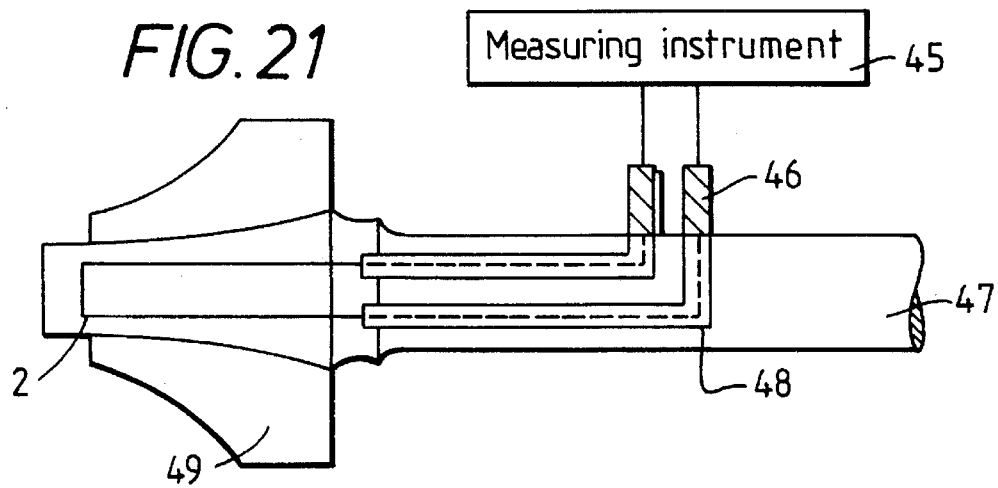
FIG. 21 is a sectional view for a ceramic turbo-charger rotor for an automobile embodying the invention.

To manufacture a turbo-charger rotor (FIG. 21) embodying the invention, one part by weight of triethanolamine and 65 parts by weight of distilled water are added to 97 parts by weight of metallic $Si_3N_4$ powder having an average particle diameter of 0.1 μm, 1 part by weight of sintering agent $Y_2O_3$ and 2 parts by weight of $Al_2O_3$ and the mixture is kneaded. It is then shaped into a turbo charger rotor blade part 49 (for a 2000 cc engine) by mold casting. At the time of molding, a bundle of 100 carbon fibers (100 μm in diameter, 5 cm in length) is incorporated into the rotor as a conductive element 2 for life diagnosis, as shown in FIG. 21.

The molded body is heated at a temperature rise rate of 1° C./min. up to 1750° C. in a furnace in nitrogen atmosphere and held at 1750° C. for two hours. Then it is cooled in the furnace to obtain the reaction sintered $Si_3N_4$ ceramic body. The binder is degreased during the temperature rise. This blade part 49 is then fixed to a metal shaft 47 containing insulating sleeves 48 of alumina. Via these sleeves 48, slip rings and carbon brushes 46 the terminals of the element 2 are was connected to an external resistance measuring instrument 45.

This turbo-charger rotor is then tested in an acceleration test. Change in resistance of the element 2 occurs upon damage of the ceramic part and is detected, thereby allowing a rotor fault to be notified to an operator.

EMBODIMENT 17

Figure 22:
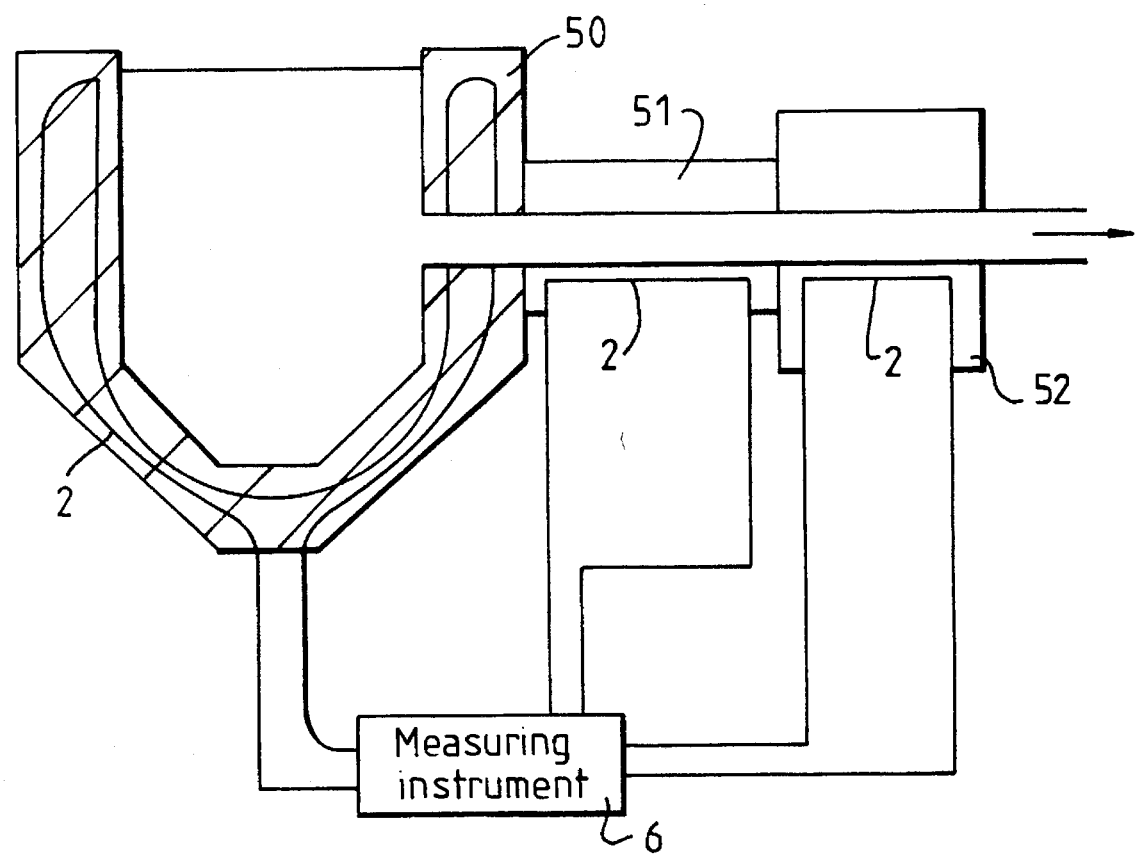
FIG. 22 is a diagram of continuous casting equipment embodying the invention.

To manufacture ceramic parts for a continuous metal casting machine (FIG. 22), one part by weight of triethanolamine and 65 parts by weight of distilled water are added to 50 parts by weight of $ZrO_2$ powder, 30 parts by weight of $SiO_2$ powder and 20 parts by weight of $Al_2O_3$ powder, and mixed. This material is used to manufacture the metal melting tundish 50, casting die inlet refractory 51 and casting die 52 of the continuous casting machine of FIG. 22. At the time of molding, a bundle of 100 SiC fibers (100 μm in diameter, 50 cm in length) is incorporated into each of these parts as a conductive element 2 whose resistance can be measured for life diagnosis.

In each case, the material is shaped in a mold and the molded body is heated at a temperature rise rate of 5° C./min. up to 1650° C. in an oxidizing atmosphere, and is held at 1650° C. for two hours. Then it is cooled in the furnace, to obtain the ceramic body provided with the conductive element. The binder is degreased during the temperature rise. Terminals of the conductive element 2 are connected to an external measuring instrument 6 by means of copper wire, and the elements 2 are insulated as required by $Al_2O_3$ tube.

In a test, change in resistance of the elements 2 was detected upon cracking of the ceramic parts due to deterioration, thereby allowing information, e.g. the residual life of the parts, to be notified to an operator. This ensures effective maintenance of the continuous casting equipment.

EMBODIMENT 18

Figure 23:
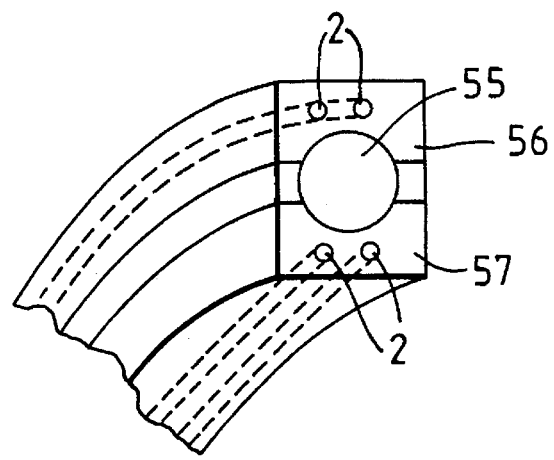
FIG. 23 is a perspective partial sectional view of a bearing part embodying the invention.

To manufacture ceramic bearing parts of the invention (FIG. 23), 13 parts by weight of a mixture of polyethylene, stearic acid and synthetic wax is added to 95 parts by weight of $Si_3N_4$ powder having an average particle diameter of 1 μm, three parts by weight of $Al_2O_3$ powder and 2 parts by weight of $Y_2O_3$, and this mixture is kneaded. It is then made into a inner and outer races 56, 57 of a ball bearing 50 mm in diameter in an injection molding machine. A composite long fiber (1.5 mm in diameter) comprising carbon fibers (10 μm in diameter, 1000 μm in length), $Al_2O_3$ fibers (5 μm in diameter, 1000 μm in length) and SiC fibers (10 μm in diameter and 100 μm in length) is employed as conductive elements 2 for life diagnosis in the inner and outer races of this bearing. The mixing ratio of the carbon, $Al_2O_3$ and SiC fibers is 50 to 30 to 20 vol percent.

After shaping, each molded body is heated at a temperature rise rate of 5° C./min. up to 1750° C. in an atmosphere of nitrogen, held for 1 hour at that temperature and cooled in the furnace to obtain an $Si_3N_4$ ceramic body provided with the elements 2. The binder is degreased during the temperature rise. Copper wire is then brazed on the terminals of the elements 2 and connected to an external resistance measuring instrument. These ceramic bearing parts are applied to the spindle of a machine tool. Change in the resistances of the elements 2 appeared when the surface of ceramic parts contacting the bearing balls was worn and damaged in a rotational test.

The invention is applicable in this manner not only to ball bearings but also to a great variety of bearings. It is also applicable for example to the mechanical seal parts of a pump which are subjected to wear, and other parts such as a slurry transport ball valve, a nozzle, a pump stator and rotor, a pump casing, and a pump shaft.

EMBODIMENT 19

FIG. 24 shows a ceramic body of the invention, usable for example as a combustor tile and in many other applications, having a three-dimensional matrix of conductive elements 2 arranged in layered planes embedded in it. The array of elements 2 in each plane is perpendicular to the array of elements 2 in the next upper and lower planes of the matrix. The body is made by sintering a laminate of green sheets carrying the respective arrays of elements 2. The body 1 is 150 mm square and 10 mm thick. Each element 2 is 1 mm wide and 0.1 mm thick.

To make the body of FIG. 24, nine parts by weight of binder comprising the polyethylene thermoplastic resin, stearic acid and synthetic wax is added to 100 parts of weight of a mixture of 50 vol percent of the metallic Si powder having an average particle diameter of 0.5 μm and 50 vol percent of the conductive TiN powder having an average particle diameter of 3 μm, and kneaded to make a conductive material A for the elements 2. Nine parts by weight of the same binder comprising the polyethylene thermoplastic resin, stearic acid and synthetic wax is added to 100 parts of weight of a mixture of 50 vol percent of the metallic Si powder having an average particle diameter of 0.5 μm and 50 vol percent of the $Al_2O_3$ powder having an average particle diameter of 10 μm, and kneaded to make a ceramic material B for the sheets which carry the elements 2.

The material B is extruded into the sheets and the material A is applied for the elements 2. The sheets are stacked into a body. The body is heated at a temperature rise rate of 1° C./min. up to 1350° C. in a nitrogen atmosphere, held for 1 hour at 1350° C. and cooled in the furnace to obtain reaction sintered composite ceramic body of FIG. 24. In this process the conductive elements 2 and material B are integrated with each other by reaction sintering; therefore, almost no residual stress occurs between the conductive elements and the material B. In the reaction sintering method almost no shrinkage occurs during firing; this allows easy production of the parts having complicated forms.

To provide heat resistance, a compact 0.3 mm-thick $ZrO_2$ film is formed on the surface of the reaction sintered composite ceramic obtained. Since the surface of the reaction sintered material is porous, $ZrO_2$ is also formed in the pores, and the film adheres strongly. Tungsten wire is then brazed on the terminals of the elements 2, and is connected to an external resistance measuring instrument 6.

This ceramic part is applied to the inner lining parts of a combustor. In combustion testing, the change in resistance occurred when the $ZrO_2$ film of the ceramic parts was damaged; this enables diagnosis of the damage location.

Conductive compounds such as ZrN, TiC, ZrC, VN, $TiB_2$, $ZrB_2$, $Cr_2N$ and TaN can be used in place of TiN, in this embodiment.

FIGS. 25 to 30 are enlarged diagrammatic views of various preferred forms of the conductive elements 2 whose resistance varies in the ceramic bodies of the invention.

Figure 27:
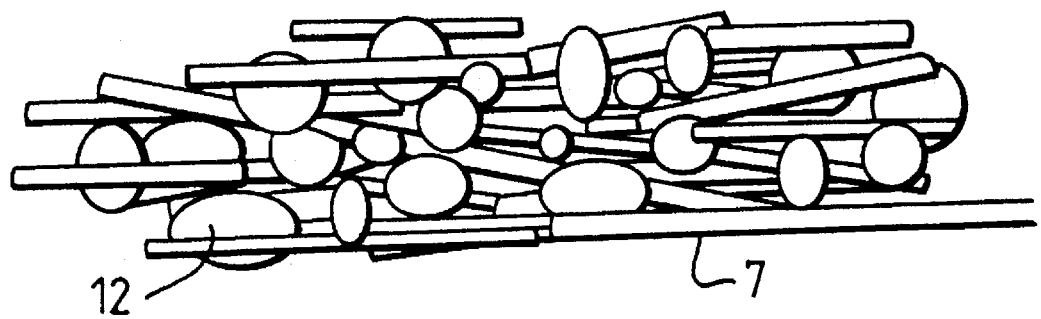
FIG. 27 is an explanatory view of yet another form of conductive element used in the invention.
Figure 28:
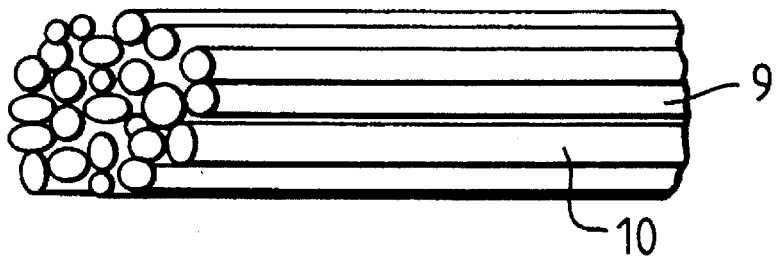
FIG. 28 is a perspective partial view of a further form of conductive element used in the invention.
Figure 29:
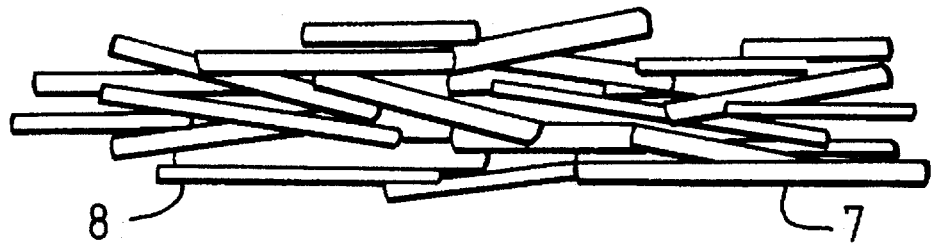
FIG. 29 is an explanatory view of a further form of conductive element used in the invention.
Figure 30:
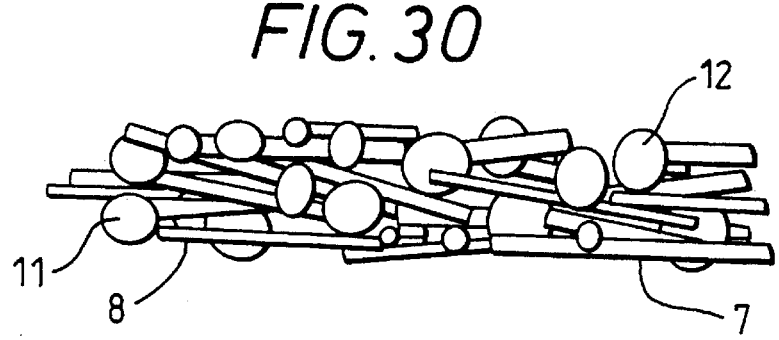
FIG. 30 is an explanatory view of a further form of conductive element used in the invention.

FIG. 25 shows a conductive element in the form of a bundle entirely of long conductive fibers 9, generally parallel to each other. FIG. 26 shows a conductive element consisting of a bundle of short electrically conductive fibers (whiskers) 7. The conductive element of FIG. 27 is a bundle of short electrically conductive fibers (whiskers) 7 with insulating particles 12 interspersed among them. The conductive element of FIG. 28 is a bundle of long electrically conductive fibers 9 and long insulating fibers 10, while that of FIG. 29 is formed of short electrically conductive fibers (whiskers) 7 and short insulating fibers (whiskers) 8. Finally, FIG. 30 shows an electrically conductive element made up of short conductive fibers (whiskers) 7 and short insulating fibers (whiskers) 8 having both conductive particles 11 and insulating particles interspersed among them. There may be a large number of fibers (whiskers) in the cross section of the element.

EMBODIMENT 20

Figure 31:
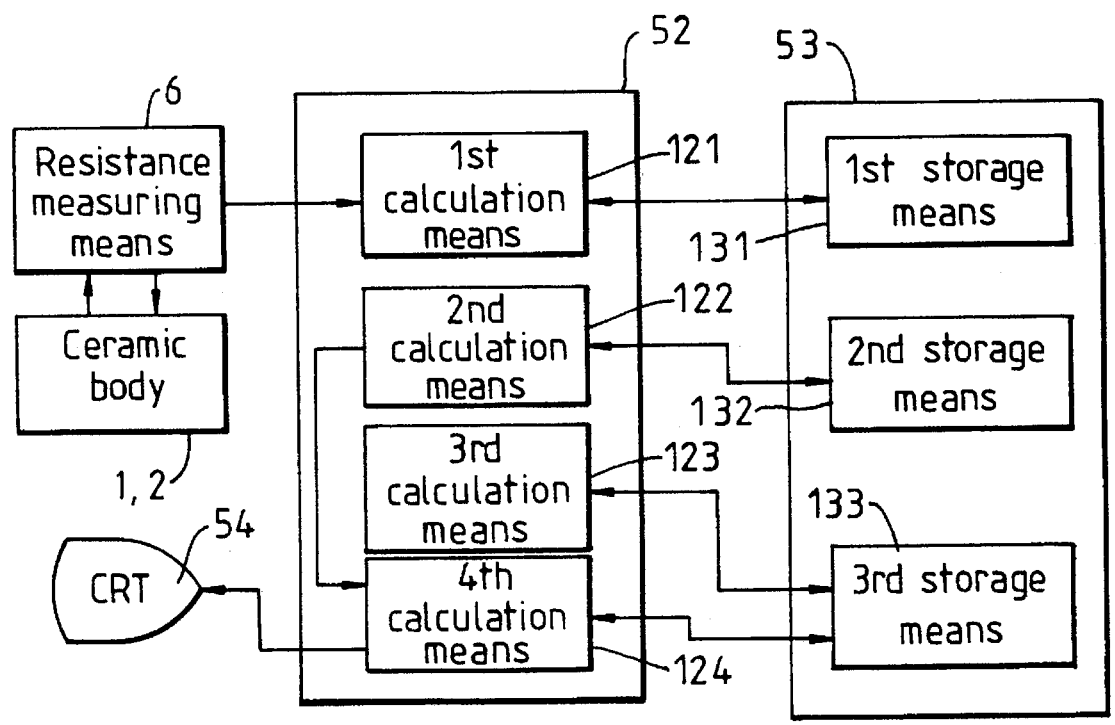
FIG. 31 is a block diagram of an apparatus including monitoring means embodying the invention.

As illustrated in FIG. 31, means for calculating residual life in apparatus of the invention may comprise a data storage device 53 which stores specified information in advance, calculation device 52 to carry out the specified calculation according to the programs and output means such as a CRT 54 which displays the residual life given by calculation device 53.

Storage device 53 comprises: (1) a first storage means 131 which stores in advance the relationship between the change of the electric resistance of the conductive element of the ceramic body and for example the amount of embrittlement representing the degree of embrittlement caused by exposure of this body to high temperature or irradiation by particles such as neutrons, (2) a second storage means 132 which stores in advance the relationship between the high temperature or irradiation of particles for the body and the amount of embrittlement, as well as the amount of use corresponding to the critical amount of embrittlement at which this specimen starts to break, and (3) a third storage means 133 which stores in advance the relationship between the high temperature or number of irradiated particles for a test piece having almost the same composition as the said body, and the time period of exposure of said test piece to the high temperature or irradiation of particles.

Figure 33A:
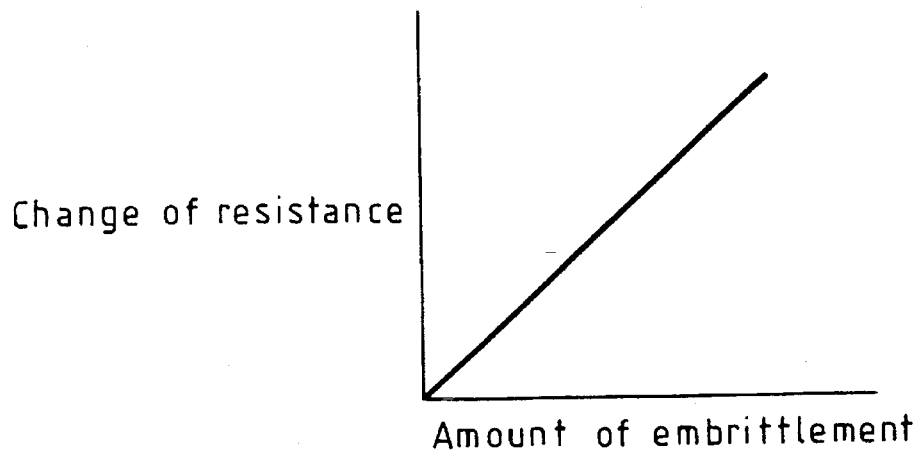
FIGS. 33(a), 33(b) and 33(c) are graphs illustrating calculation of a critical period of use of a ceramic part.
Figure 33B:
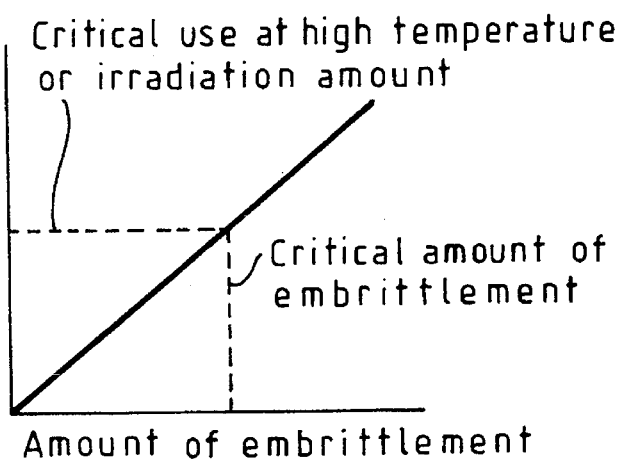
Figure 33C:
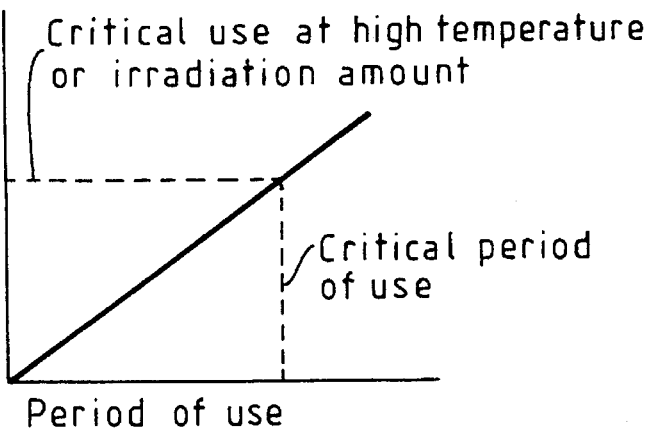

The contents stored in storage device 53 will be explained with reference to FIG. 33. FIG. 33 (a) is a graph denoting the data in the first storage means, where the vertical axis denotes the change in resistance of the conductive element, while the horizontal axis shows the amount of embrittlement. The change in electric resistance shown by the vertical axis and the volume of embrittlement shown by the horizontal axis relate to the ratio of crack formation before and after exposure to the high temperature or irradiation of particles (i.e. breaking strength after the exposure to high temperature or irradiation of particles relative to breaking strength before such exposure).

FIG. 33 (b) is a graph showing the contents in the second storage means; the vertical axis shows use at high temperature or number of particles irradiated onto the specimen, while the horizontal axis shows the amount of embrittlement. The critical amount of embrittlement shown relates to the amount of embrittlement when critical cracking occurs.

FIG. 33 (c) is the graph showing the contents of the third storage means. The vertical axis represents amount of use of high temperature or irradiated amount, while the horizontal axis shows the time period of use, where the critical time period of use is defined as the time period of use corresponding to the critical use at high temperature or irradiation amount.

Calculation device 53 consisting of a CPU comprises: (1) a first calculation means 121 to obtain from the first storage device the amount of embrittlement corresponding to the measured change in resistance of the test piece, (2) a second calculation means 123 to obtain from the second storage means the amount of use at high temperature or irradiated amount for the test piece corresponding to the amount of embrittlement obtained from the first calculation means, (3) a third calculation means 123 to obtain from the third storage means the calculated time period of use for the test piece, corresponding to the amount of use at high temperature or irradiated amount obtained from the second calculation means, and (4) a fourth calculation means 124 to obtain from the third storage means the critical time period of use corresponding to the critical amount stored in the second storage means, to compare this critical time period of use to the calculated time period of use, and to calculate either the difference between the two or their ratio.

Figure 32:
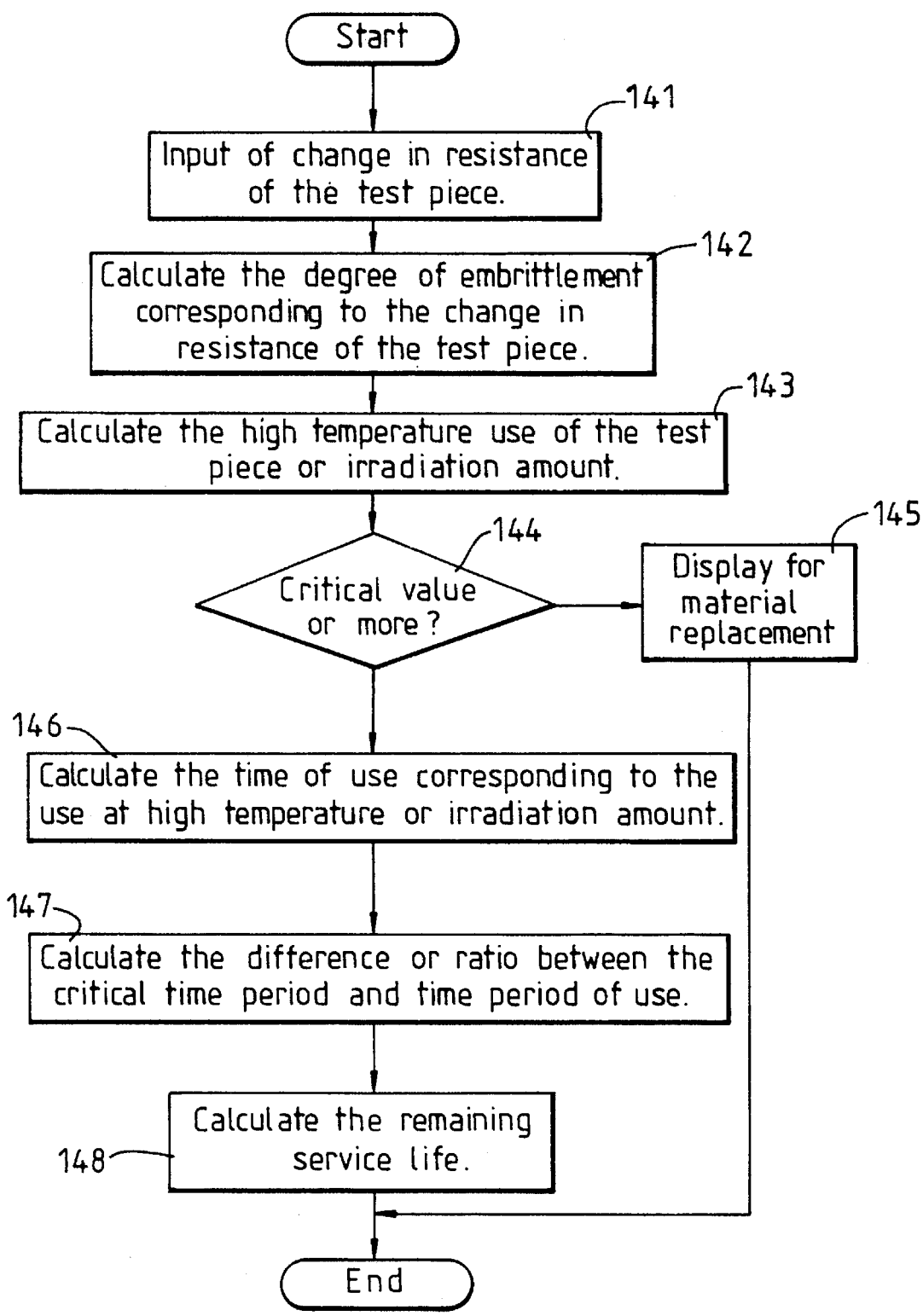
FIG. 32 is a flow chart for a method of calculating service life embodying the invention.

This method will be explained with reference to the flow chart given in FIG. 32. The first step 141 is to input the change in resistance of the test piece exposed to high temperature or irradiation by particles. The second step 142 is to obtain the amount or degree of embrittlement corresponding to the change in resistance of the test piece from the first storage means which stores a predetermined relationship between these values in material which has the same composition as that of the test piece. The third step 143 is to obtain the amount of use or amount of irradiation for the test piece corresponding to the amount of embrittlement of the test piece, from the second storage means which stores a predetermined relationship between these values. In the fourth step 144, if the amount of use or amount of irradiation of the test piece has exceeded the critical volume, this information is output to display the need for replacement of the body (step 145). If the amount of use or amount of irradiation of the test piece is below the critical value, the calculated time period of use corresponding to the amount of use or irradiation is obtained, from the third storage means which stores in advance the known relationship of these values (step 146). The final step is to obtain either the difference between the calculated time period of use and the critical time period of use or their ratio, or both of them (step 148).

The above embodiments are given by way of example only and do not limit the scope of the invention.

What is claimed is:

1. A ceramic body which in use is subjected to stress and undergoes gradual change with time as a result of said stress, said ceramic body comprising (a) a sintered ceramic material and (b) a service life and maintenance diagnosis circuit for diagnosing and estimating service life and maintenance need, said service life and maintenance diagnosis circuit including at least one electrically conductive element in contact with said sintered ceramic material, said service life and maintenance diagnosis circuit including components of electrically conducting material and components of electrically insulating refractory material, said at least one electrically conductive element being positioned at a region of the sintered ceramic material which undergoes said gradual change with time as a result of said stress, said at least one electrically conductive element having a measurable electrical resistance which is increased irreversibly in dependence on said gradual change of said ceramic body, said service life and maintenance diagnosis circuit including at least one composite material selected from the group consisting of (1) carbon and $Al_2O_3$, (2) carbon and SiC, (3) SiC and $Al_2O_3$, and (4) carbon, SiC and $Al_2O_3$.

2. A ceramic body according to claim 1 wherein said structural change is formation of cracks.

3. A ceramic body according to claim 1, wherein said components of electrically conducting material and said components of electrically insulating refractory material are in a form selected from the group consisting of fibers and whiskers.

4. A ceramic body which in use is subjected to stress and undergoes gradual change with time as a result of said stress, said ceramic body comprising (a) a sintered ceramic material and (b) a service life and maintenance diagnosis circuit for diagnosing and estimating service life and maintenance need, said service life and maintenance diagnosis circuit including an electrically conductive element at a region of said sintered ceramic material which is structurally changed by said stress, said service life and maintenance diagnosis circuit including components of electrically conducting material and components of electrically insulating refractory material, said electrically conductive element comprising as seen in cross-section, at least 100 elongate members selected from fibers and whiskers, said electrically conductive element undergoing an irreversible increase in electrical resistance in dependence upon structural change of said sintered ceramic material caused by said stress, said service life and maintenance diagnosis circuit including at least one composite material selected from the group consisting of (1) carbon and $Al_2O_3$, (2) carbon and SiC, (3) SiC and $Al_2O_3$, and (4) carbon, SiC and $Al_2O_3$.

5. A ceramic body which in use is subjected to stress and undergoes gradual change with time as a result of said stress, said ceramic body comprising (1) a sintered ceramic material and (2) at least one service life and maintenance diagnosis circuit in contact with said sintered ceramic material, said at least one service life and maintenance diagnosis circuit including at least one electrically conductive element in contact with said sintered ceramic material, said at least one service life and maintenance diagnosis circuit including components of electrically conducting material and components of electrically insulating refractory material, said at least one service life and maintenance diagnosis circuit having a measurable electrical resistance which is increased irreversibly in dependence on said gradual change of said sintered ceramic material, said at least one service life and maintenance diagnosis circuit being positioned at a region of said sintered ceramic material which undergoes the gradual change with time as a result of the stress, whereby service life and maintenance diagnosis are performed in accordance with an increase in said electrical resistance, said at least one service life and maintenance diagnosis circuit including at least one composite material selected from the group consisting of (1) carbon and $Al_2O_3$, (2) carbon and SiC, (3) SiC and $Al_2O_3$, and (4) carbon, SiC and $Al_2O_3$.

6. A ceramic body according to claim 5, wherein said components of electrically conducting material and said components of electrically insulating refractory material are in a form selected from the group consisting of fibers and whiskers.

7. A ceramic body which in use is subjected to stress and undergoes gradual change with time as a result of said stress, said ceramic body comprising (1) a sintered ceramic material and (2) at least one service life and maintenance diagnosis circuit, for diagnosing and estimating service life and maintenance need, at a region of said sintered ceramic material which is structurally changed by said gradual stress, said at least one service life and maintenance diagnosis circuit including components of electrically conducting material and components of electrically insulating refractory material, said at least one service life and maintenance diagnosis circuit comprising, as seen in cross-section, at least 100 elongate members selected from fibers and whiskers, said at least one service life and maintenance diagnosis circuit undergoing an irreversible increase in electrical resistance in dependence upon structural change of the sintered ceramic material caused by said gradual stress, said service life and maintenance diagnosis circuit including at least one composite material selected from the group consisting of (1) carbon and $Al_2O_3$, (2) carbon and SiC, (3) SiC and $Al_2O_3$, and (4) carbon, SiC and $Al_2O_3$.

8. A ceramic body which in use is subjected to stress and undergoes gradual change with time as a result of said stress, said ceramic body comprising (a) a sintered ceramic material and (b) a service life and maintenance diagnosis circuit for diagnosing and estimating service life and maintenance need, said service life and maintenance diagnosis circuit including at least one electrically conductive element in contact with said sintered ceramic material, said service life and maintenance diagnosis circuit including components of electrically conducting material and components of electrically insulating refractory material, said at least one electrically conductive element being located in a region of the ceramic body which undergoes said gradual change, said at least one electrically conductive element having a measurable electrical resistance which is increased irreversibly in dependence on said gradual change of said ceramic body, said at least one electrically conductive element consisting of material having a bulk electrical resistance of not more than 1 $\Omega$cm, said at least one electrically conductive element, as seen in cross-section, comprising a bundle of elongate members selected from the group consisting of fibers and whiskers, said service life and maintenance diagnosis circuit including at least one composite material selected from the group consisting of (1) carbon and $Al_2O_3$, (2) carbon and SiC, (3) SiC and $Al_2O_3$, and (4) carbon, SiC and $Al_2O_3$.

9. A ceramic body according to claim 8 wherein on average, as seen in cross-section, said electrically conductive element comprises a number of said elongate members in the range 100 to $10^5$.

10. A ceramic body according to claim 8 wherein said bundle of elongate members is selected from a mixture of insulating and conductive fibers and a mixture of insulating and conductive whiskers.

11. A ceramic body according to claim 8 wherein said bundle comprises additionally particles selected from electrically insulating particles and electrically conductive particles.

12. A ceramic body which in use is subjected to stress and undergoes gradual change with time as a result of said stress, said ceramic body comprising (a) a sintered ceramic material and (b) a service life and maintenance diagnosis circuit for diagnosing and estimating service life and maintenance need, said service life and maintenance diagnosis circuit including at least one electrically conductive element in contact with said sintered ceramic material, said at least one electrically conductive element having a measurable electrical resistance which is increased irreversibly in dependence on said gradual change of said ceramic body, said at least one electrically conductive element also constituting a heating element of said ceramic body.

13. A ceramic body which in use is subjected to stress and undergoes gradual change with time as a result of said stress, said ceramic body comprising (a) a sintered ceramic material and (b) a service life and maintenance diagnosis circuit for diagnosing and estimating service life and maintenance need, said service life and maintenance diagnosis circuit including at least one electrically conductive element in contact with said sintered ceramic material, said at least one electrically conductive element having a measurable electrical resistance which is increased irreversibly in dependence on said gradual change of said ceramic body, said service life and maintenance diagnosis circuit further including a metallic wire overlaying a surface of said sintered ceramic material, said metallic wire providing heat resistance.

14. A ceramic body which in use is subjected to stress and undergoes gradual change with time as a result of said stress, said ceramic body comprising (1) a sintered ceramic material and (2) at least one service life and maintenance diagnosis circuit in contact with said sintered ceramic material, said at least one service life and maintenance diagnosis circuit having a measurable electrical resistance which is increased irreversibly in dependence on said gradual change of said sintered ceramic material, whereby service life and maintenance diagnosis are performed in accordance with an increase in said electrical resistance, wherein the at least one service life and maintenance diagnosis circuit also constitutes a heating element of the ceramic body.

15. A ceramic body which in use is subjected to stress and undergoes gradual change with time as a result of said stress, said ceramic body comprising (1) a sintered ceramic material and (2) at least one service life and maintenance diagnosis circuit, for diagnosing and estimating service life and maintenance need, at a region of said sintered ceramic material which is structurally changed by said stress, said at least one service life and maintenance diagnosis circuit comprising, as seen in cross-section, at least 100 elongate members selected from fibers and whiskers, wherein the at least one service life and maintenance diagnosis circuit also constitutes a heating element of the ceramic body.

* * * * *